(12) United States Patent
Atanasova et al.

(10) Patent No.: US 9,346,971 B2
(45) Date of Patent: May 24, 2016

(54) POLYMER COATING COMPRISING 2-METHOXYETHYL ACRYLATE UNITS SYNTHESIZED BY SURFACE-INITIATED ATOM TRANSFER RADICAL POLYMERIZATION

(75) Inventors: Katja Jankova Atanasova, Lyngby (DK); Soren Hvilsted, Horsholm (DK); Charlotte Juel Fristrup, Virum (DK)

(73) Assignee: Technical University of Denmark, Lyngby (DK)

( * ) Notice: Subject to any disclaimer, the term of this patent is extended or adjusted under 35 U.S.C. 154(b) by 493 days.

(21) Appl. No.: 13/384,130

(22) PCT Filed: Jul. 14, 2010

(86) PCT No.: PCT/DK2010/050187
§ 371 (c)(1),
(2), (4) Date: Apr. 4, 2012

(87) PCT Pub. No.: WO2011/006507
PCT Pub. Date: Jan. 20, 2011

(65) Prior Publication Data
US 2012/0184029 A1    Jul. 19, 2012

Related U.S. Application Data

(60) Provisional application No. 61/225,840, filed on Jul. 15, 2009.

(30) Foreign Application Priority Data

Jul. 15, 2009   (EP) ..................... 09165556

(51) Int. Cl.
*C09D 133/06*   (2006.01)
*A61L 27/34*    (2006.01)
(Continued)

(52) U.S. Cl.
CPC ............. *C09D 133/062* (2013.01); *A61L 27/34* (2013.01); *A61L 31/10* (2013.01);
(Continued)

(58) Field of Classification Search
USPC ......................................................... 427/302
See application file for complete search history.

(56) References Cited

U.S. PATENT DOCUMENTS 3,935,368 A * 1/1976 Weiss ................. D06N 3/08
427/393.5
5,202,025 A * 4/1993 Onishi et al. ............. 210/500.35
(Continued)

FOREIGN PATENT DOCUMENTS

EP    0 420 765 B1    11/1995
EP    2439214         4/2012
(Continued)

OTHER PUBLICATIONS

Bednarek M. et al., Novel Polymers Based on Atom Transfer Radical Polymerization of 2-Methoxyethyl Acrylate, J. Polym. Sci. Pol. Chem., 45: 333-340, 2007.
(Continued)

*Primary Examiner* — Nathan T Leong
(74) *Attorney, Agent, or Firm* — Dinsmore & Stohl LLP

(57) ABSTRACT

The present invention relates to preparation of a polymer coating comprising or consisting of polymer chains comprising or consisting of units of 2-methoxyethyl acrylate synthesized by Surface-Initiated Atom Transfer Radical Polymerization (SI ATRP) such as ARGET SI ATRP or AGET SI ATRP and uses of said polymer coating.

9 Claims, 11 Drawing Sheets

(51) Int. Cl.
*A61L 31/10* (2006.01)
*A61B 17/06* (2006.01)
*A61B 19/02* (2006.01)
*A61B 17/00* (2006.01)
*A61M 5/178* (2006.01)

(52) U.S. Cl.
CPC ......... *A61B17/06066* (2013.01); *A61B 19/026* (2013.01); *A61B 2017/00889* (2013.01); *A61B 2017/00955* (2013.01); *A61B 2017/00995* (2013.01); *A61M 5/178* (2013.01); *Y10T 428/1334* (2015.01); *Y10T 428/1352* (2015.01); *Y10T 428/1393* (2015.01); *Y10T 428/31649* (2015.04); *Y10T 428/31935* (2015.04)

(56) References Cited

U.S. PATENT DOCUMENTS

| | | | |
|---|---|---|---|
| 6,286,955 | B1 | 9/2001 | Akashi |
| 6,288,955 | B1 | 9/2001 | Shibano et al. |
| 2006/0013853 | A1* | 1/2006 | Richard ............ 424/423 |
| 2012/0184029 | A1* | 7/2012 | Atanasova et al. ..... 435/304.1 |

FOREIGN PATENT DOCUMENTS

| | | |
|---|---|---|
| JP | 2006-172424 | 1/2008 |
| JP | 2008001794 A | 1/2008 |
| JP | 2008-146951 | 12/2009 |
| WO | 96/30421 A1 | 10/1996 |
| WO | WO-2006/014604 | 2/2006 |
| WO | WO-2008019450 | 2/2008 |
| WO | WO-2010140372 | 12/2010 |

OTHER PUBLICATIONS

Brar A.S. et al., Atom Transfer Radical Polymerization of 2-methoxy Ethyl Acrylate and its Block Copolymerization with Acrylonite, Eur. Polym. J., 43: 1046-1054, 2007.
Fristrup C.J. et al., Surface-initiated Atom Transfer Radical Polymerization: A Technique to Develop Biofunctional Coatings, submitted to "Soft Matter," 2009.
Xu F.J. et al. Bioactive Surfaces and Biomaterials Via Atom Transfer Radical Polymerization, Progress in Polymer Science (article in press), 43 pages, 2009.
Gunaydin S. et al., Clinical Performance and Biocompatibility of Poly(2-Methoxyethylacrylate)-Coated Extracorporeal Circuits, Ann. Thorac. Surg., 74: 819-824, 2002.
Hansen N.M.L. et al., Fluorinated Bio-Acceptable Polymers Via an ATRP Macroinitiator Approach, J. Polym. Sci. Pol. Chem., 45: 5770-5780, 2007.
Huang J. et al., Antibacterial Polypropylene Via Surface-Initiated Atom Transfer Radical Polymerization, Biomacromolecules, 8: 1396-1399, 2007.
Kato M. et al., Polymerization of Methyl Methacrylate with the Carbon Tetrachloride/Dichlorotris-(triphenylphosphine) ruthenium(II)/Methylaluminim Bis(2,6-di-tert-butylphenoxide) Initiating System: Possibility of Living Radical Polymerization, Macromolecules, 28: 1721-1723, 1995.
Noiset O. et al., Surface Reduction of Poly(aryl ether ether ketone) film: UV Spectrophotometric, 3H Radiochemical, and X-ray Photoelectron Spectroscopic Assays of the Hydroxyl Functions, Macromolecules, 30: 540-548, 1997.
Saito N. et al., Effects of New Polymer-coated Extracorporeal Circuits on Biocompatibility During Cardiopulmonary Bypass, J. Artif. Organs, 24(7): 547-554, 2000.
Suhara H. et al., Efficacy of a New Coating Material, PMEA, for Cardiopulmonary Bypass Circuits in a Porcine Model, Ann. Thorac. Surg., 71: 1603-1608, 2001.
Tanaka M. et al., Study on Kinetics of Early Stage Protein Adsorption on Oily(-methoxyethylacrylate)(PMEA) Surface, Colloid. Surface A, 195-204, 2002.
Tanaka M. et al., In Situ Studies on Protein Adsorption onto a Poly(2-methoxyethylacrylate) Surface by a Quartz Crystal Microbalance, Colloid. Surface A, 145-152, 2001.
Wang J.S. et al., Controlled/"Living" Radical Polymerization. Atom Transfer Radical Polymerization in the Presence of Transition-metal Complexes, J. Am. Chem. Soc., 117: 5614-5615, 1995.
Tsukagoshi, Surface Modification of Poly(Oligoethylene Oxide Methacrylate) for Resisting Protein Adsorption, In: Colloids and Surfaces B: Biointerfaces, 54(1): 94-100, 2007.
Nobuo, K. et al., English translation of JP 2008-46951, Surface-Hydrophilic Polyolefin Molded Article and Method for Producing It, published Dec. 17, 2009.
Nobuo, K. et al., Abstract, JP 2008-46951, Surface-Hydrophilic Polyolefin Molded Article and Method for Producing It, published Dec. 17, 2009.
Takayuki, M. et al., English translation of JP 2006-172424, Polymer Compound for Medical Material and Medical Material Using the Same Polymer Compound, published Jan. 10, 2008.
Takayuki, M. et al., Abstract, JP 2006-172424, Polymer Compound for Medical Material and Medical Material Using the Same Polymer Compound, published Jan. 10, 2008.
Fristrup, C. et al., Stability of AspB28 Insulin Exposed to Modified and Unmodified Polypropylene, *Protein & Peptide Letters*, 22(7): 1-9, 2015.
Hansson, S. et al., ARGET ATRP for Versatile Grafting of Cellulose using Various Monomers, *Applied Materials and Interfaces*, 1(11): 2651-59, 2009.
Jakubowski, W. et al., Activators Regenerated by Electron Transfer for Atom Transfer Radical Polymerization of Styrene, *Macromolecules*, 39: 39-45, 2006.
Yamamoto, S. et al., Temperature and pH-Responsive Dense Copolymer Brushes Prepared by ATRP, *Macromolecules*, 41: 7013-20, 2008.

* cited by examiner

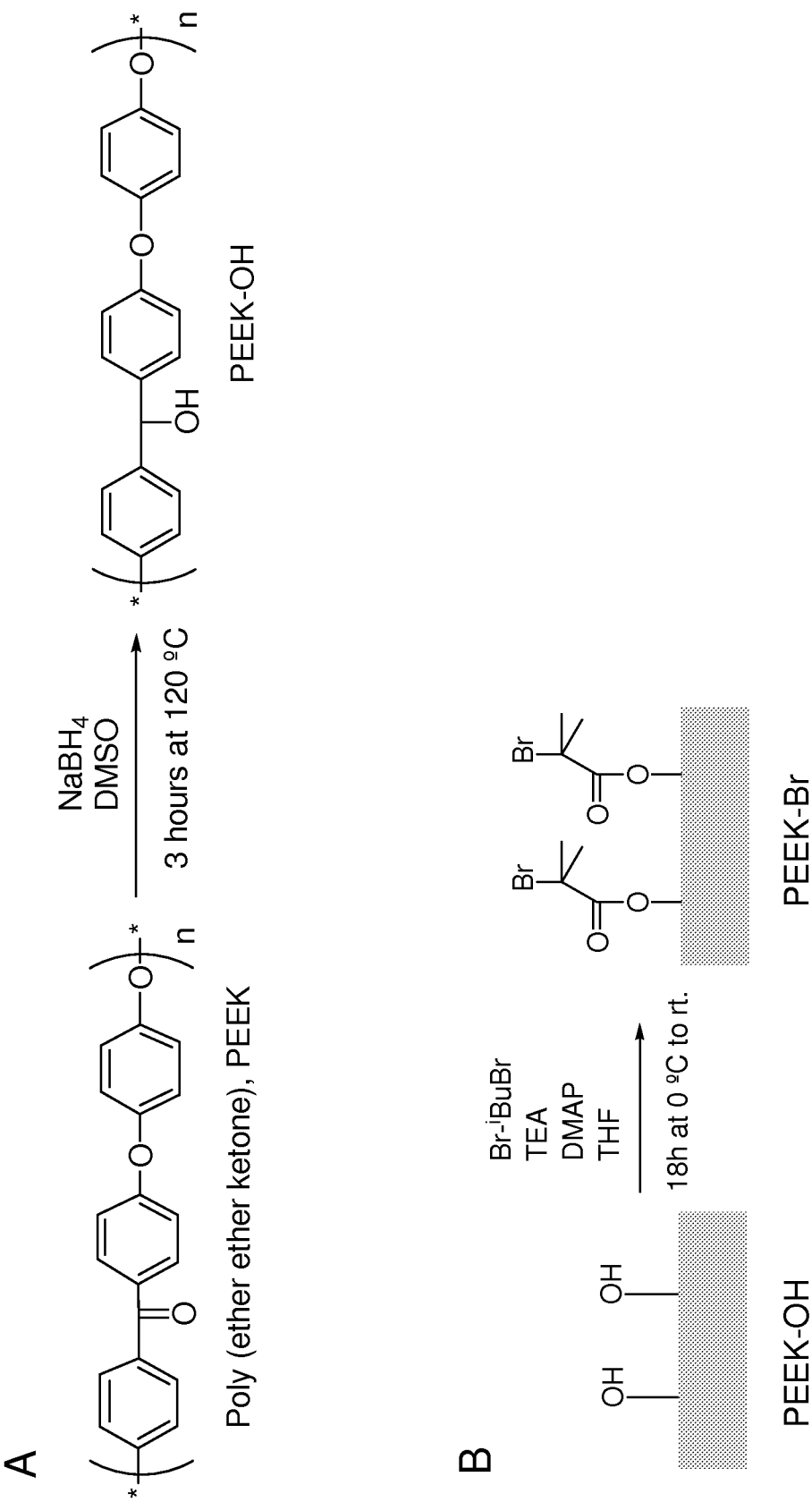

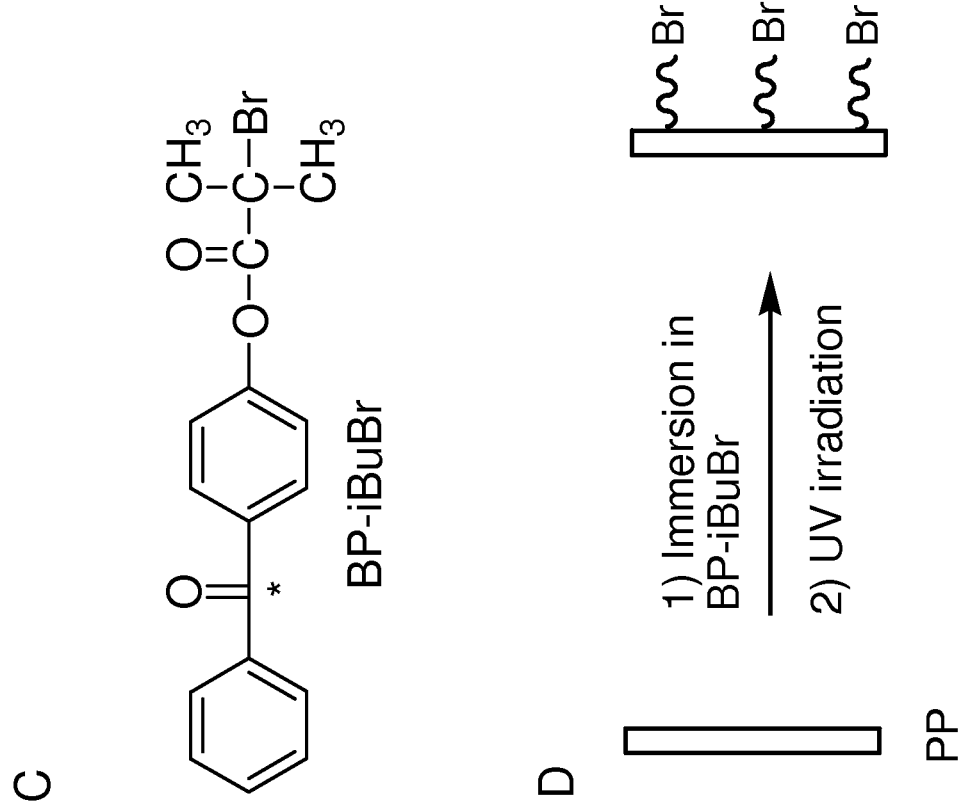

Figure 6
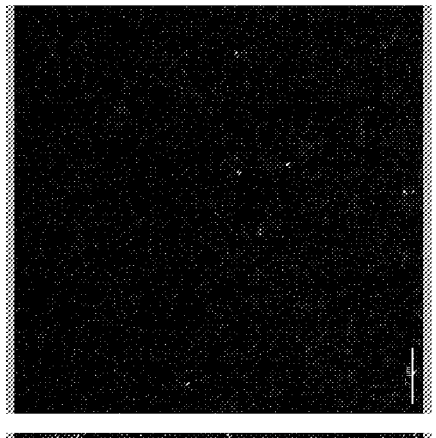
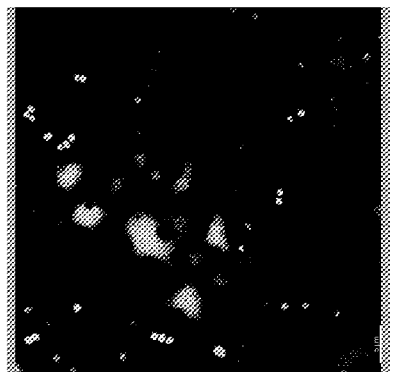
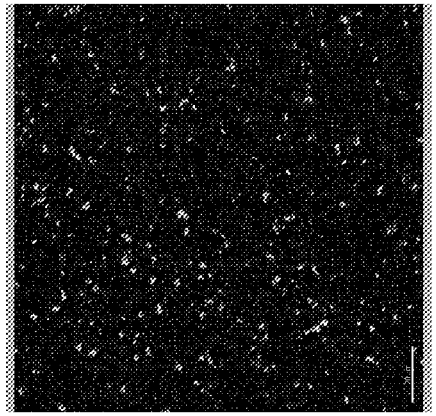
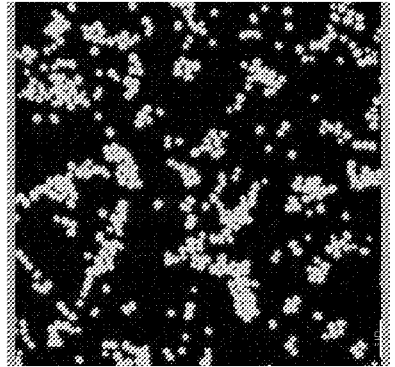

POLYMER COATING COMPRISING 2-METHOXYETHYL ACRYLATE UNITS SYNTHESIZED BY SURFACE-INITIATED ATOM TRANSFER RADICAL POLYMERIZATION

CROSS-REFERENCE TO RELATED APPLICATIONS

This application is the U.S. National Phase of PCT/DK2010/050187 filed Jul. 14, 2010, which claims priority of European Patent Application 09165556.3 filed Jul. 15, 2009, and U.S. Provisional Patent Application 61/225,840 filed Jul. 15, 2009.

All patent and non-patent references cited in the present application are hereby incorporated by reference in their entirety.

FIELD OF INVENTION

Many conventional biomaterials lack the ability to properly interact with or support biological matter coming into contact with said biomaterials leading to undesired biological responses. However, these undesired responses may be controlled by altering the chemical and physical properties of the surface of said biomaterials. In this respect, surface modification represents a well known strategy of providing suitable biocompatible materials. The present invention relates to preparation of a biocompatible material comprising a polymer coating consisting of or comprising poly(2-methoxyethyl acrylate) (PMEA) synthesized by Surface-Initiated Atom Transfer Radical Polymerization (SI ATRP) such as ARGET (activator regenerated by electron transfer) SI ATRP or AGET (activators generated by electron transfer) SI ATRP and uses of said biocompatible material.

BACKGROUND OF INVENTION

Polymers have previously been synthesized by the Atom Transfer Radical Polymerization (ATRP) method. The ATRP process was introduced by Matyjaszewski and Sawamoto [1-3] using different catalyst systems. ATRP is a controlled method which converts monomers to polymers by using radical polymerization. The initiators used for ATRP are commonly simple alkyl halides. A halogen atom X is transferred during the polymerization. Moreover, a catalyst system is present which consist of a transition metal complexed by one or more ligands. The catalyst provides equilibrium between the active form and the inactive form (called the dormant state). The equilibrium is displaced towards the dormant state; therefore, the polymer chains will only be active for a short time, thus allowing for a suppression of chain termination reactions and thereby controlling the polymerization. A controlled polymerization method like ATRP will result in controlled molar masses, controlled polymer architecture, and narrow molecular weight distributions (cf. schematic illustration of ATRP in FIG. 1).

PMEA coatings have previously been disclosed including PMEA-coated cardiopulmonary bypass circuits and oxygenators [4-6]. Protein adsorption studies on PMEA have also been disclosed [7-8].

PMEA polymers have previously been made by free radical polymerisation. Homopolymerization of MEA by ATRP has e.g. previously been described [9-11]. However, previously described PMEA coating is physically adsorbed to the surface whereas the PMEA made by SI ATRP such as ARGET SI ATRP or AGET SI ATRP according to the present invention is covalently bound to the surface. The covalent bonds result in a PMEA coating with improved characteristics such as improved long-term stability.

SUMMARY OF INVENTION

The present invention relates to a polymer coating consisting of one or more repeating units of 2-methoxyethyl acrylate (MEA) covalently bound to one or more surface(s). The invention relates to a PMEA coating obtained and/or obtainable by SI ATRP such as ARGET SI ATRP or AGET SI ATRP.

In another embodiment the present invention relates to a device comprising one or more surface(s) covalently bound to repeating units of 2-methoxyethyl acrylate (MEA). Said device can be a container (such as a bottle, flask, box, bag, or ampoule), an implantable device (such as a stent, or pump), a tubing device, a membrane, a film, or a medical device (such as an infusion set, a dialysis device, a catheter or a pump).

The present invention further relates to methods for making a PMEA coating by SI ATRP such as ARGET SI ATRP or AGET SI ATRP.

In one embodiment said SI ATRP such as ARGET SI ATRP or AGET SI ATRP method comprises one or more of the steps of i) use of initiator groups covalently bound to one or more surface(s) of a substrate
ii) adding one or more catalyst(s), one or more ligand(s), 2-methoxyethyl acrylate and optionally one or more solvent(s) to a reaction container comprising one or more substrate(s) with one or more surface(s) comprising said initiator groups
iii) allowing the reaction to take place; and optionally
iv) use of one or more reducing agents
thereby making a PMEA coating covalently attached to the surface of the substrate.

The present invention also relates to use of a coating of PMEA covalently bound to one or more surface(s). Said coating can be used for contacting one or more subject matters selected from the group consisting of one or more protein(s), one or more peptide(s), one or more body liquids, one or more tissues, and meat. The one or more body liquids can be selected from the group consisting of blood, blood plasma, serum, amniotic fluid, aqueous humour, cerumen, Cowper's fluid or pre-ejaculatory fluid, chyme, female ejaculate, interstitial fluid, lymph, breast milk, mucus (including nasal drainage and phlegm), pleural fluid, pus, saliva, sebum (skin oil), semen, sweat, tears, urine, vaginal secretion and vomit.

In one preferred embodiment the present invention also relates to use of a coating of PMEA covalently bound to one or more surface(s) for contacting such as during storage blood such as whole blood or fractions of blood. Blood fractionation is the process of fractionating whole blood, or separating it into its component parts. This fractionation can in one embodiment be performed by centrifugation of the blood.

The resulting components of blood fractionation are in one embodiment:
  a clear solution of blood plasma in the upper phase,
  the buffy coat, which is a thin layer of leukocytes (white blood cells) mixed with platelets in the middle, and
  erythrocytes (red blood cells) at the bottom of the centrifuge tube.

The PMEA coating according to the present invention can be used for storage or contacting of any of these blood fractions or mixtures thereof.

The PMEA coating according to the present invention can be used for storage or contacting of any of the following samples:

Plasma protein(s) or plasma protein mixtures e.g. including albumin and/or, immunoglobulins, and/or clotting proteins such as fibrinogen.

Plasma protein(s) or plasma protein mixtures for clinical use and/or therapeutic uses.

Plasma components for clinical use such as factor VIII, factor IX complex, immunoglobulin, antithrombin III, alpha-1-antitrypsin purified plasma component for injection or transfusion.

Plasma or plasma proteins or plasma components for analytical uses

Plasma containing one or more biomarkers that can play a role in clinical diagnosis of diseases Plasma for clinical diagnosis The PMEA coating according to the present invention can be used for limitation or prevention of bacterial growth. The PMEA coating can be used for bacteria repelling.

The PMEA coating can also be used for long terms as it has long term stability. Accordingly, the PMEA coating can e.g. be used for coating of a device used for long term storage of a suitable material (e.g. any of the materials mentioned in this application) for more than 1 months, more than 3 months, more than 6 months, more than 1 year, more than 5 years or more than 10 years with out significant leak of the PMEA coating into said material. With out significant leak into said material can in one embodiment mean that less than 5% of the PMEA coating is leaking into said material, such as less than 1% or less than 0.1%

DESCRIPTION OF DRAWINGS

FIG. 5: Example of preparation of initiating groups attached to surfaces of PEEK and PP, which can be used for SI ATRP

DEFINITIONS AND ABBREVIATIONS

Figure 1:
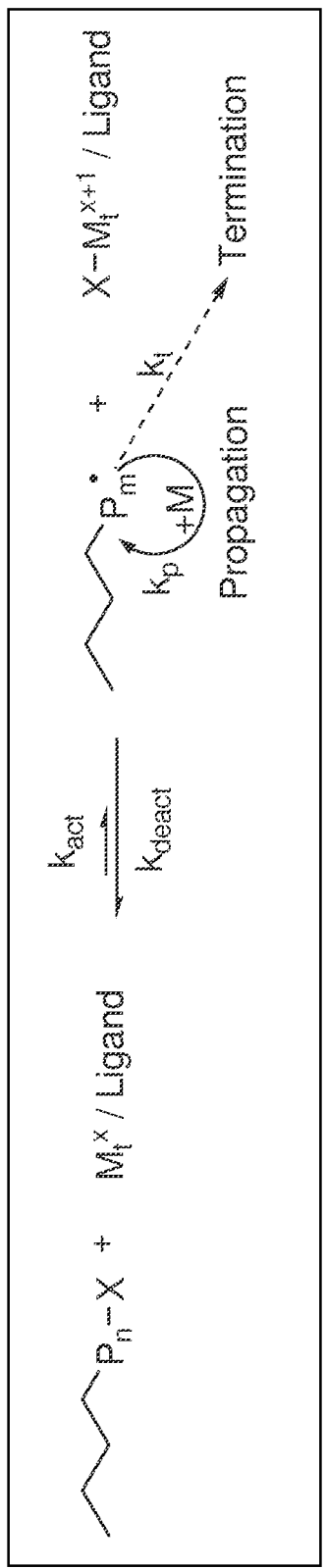
FIG. 1: Scheme showing the principle of Atom Transfer Radical Polymerization (ATRP).

ATRP is an abbreviation of Atom Transfer Radical Polymerization

Biocompatible surface: Material that, when interacting with biological material, does not disturb the biological material, e.g. without provoking a natural defensive response or e.g. does not induce an acute or chronic inflammatory response or e.g. does not prevent a proper differentiation of implant-surrounding tissues or e.g. does not affect the stability of proteins and/or peptides.

Biocompatibility as used herein means the quality of not having toxic or injurious effects on biological systems. In one embodiment biocompatibility refers to the ability of a biomaterial to perform its desired function with respect to a medical therapy, without eliciting any undesirable local or systemic effects in the recipient or beneficiary of that therapy, but generating the most appropriate beneficial cellular or tissue response in that specific situation, and optimizing the clinically relevant performance of that therapy.

Biological material: Any material derived from a living entity including plants, animals and human beings or a living part thereof, such as an organ, tissue or cell. The preferred biological system is a mammalian system, preferably a human system. The biological material includes e.g. proteins, peptides and enzymes.

Bodily fluids are liquids that are inside the bodies of animals or human beings. They include fluids that are excreted or secreted from the body as well as fluids that normally are not excreted or secreted from the body.

Container can be any type of a container with a void cavity for storage (with or without a lid) such as a bottle, flask, bag, blood bag, pot, tub, dish, tray, bowl, basin, pill bottle, medicine bottle, ampoule, flagon, syringe, needle, tube, cell culture dish or flask, tissue culture dish or flask.

Fouling: Fouling refers to the accumulation of unwanted material on a surface, e.g. in an aquatic environment. The fouling material can consist of either living organisms (biofouling) or a non-living substance (inorganic or organic). Other terms used in the literature to describe fouling include: deposit formation, encrustation, crudding, deposition, scaling, scale formation, and sludge formation. The last five terms have a more narrow meaning than fouling within the scope of the fouling science and technology.

HMTETA is an abbreviation of 1,1,4,7,10,10-hexamethyl-triethylenetetramine

Implantable device: as used herein, an implantable device may be any suitable medical substrate that can be implanted in a human or veterinary patient.

MEA is an abbreviation of 2-methoxyethyl acrylate.

A medical device is a product which is used for medical purposes in an animal or a human being in any type of diagnosis, treatment, therapy or surgery.

Membrane: Barrier between two phases and allowing transport via sorption/diffusion and/or through pores.

PEEK is an abbreviation of poly(ether ether ketone)

PMDETA is an abbreviation of 1,1,4,7,7-pentamethyldi-ethylenetriamine

PMEA is an abbreviation of poly(2-methoxyethyl acrylate).

PP is an abbreviation of polypropylene.

Prosthesis (plural prostheses) is an artificial extension that replaces a missing body part.

Ratio: a ratio mentioned herein is a mole by mole ratio unless otherwise specified.

SI ATRP is an abbreviation of Surface-Initiated Atom Transfer Radical Polymerization. In one embodiment SI ATRP can be performed without use of a reducing agent. Normal SI ATRP refers to SI ATRP performed without use of a reducing agent.

The term 'substrate' can be any material whereto the polymer according to the present invention can be covalently bound to the surface of said substrate.

AGET: activators generated by electron transfer.

AIBN: azobisisobutyronitrile.

ARGET: activator regenerated by electron transfer.

ICAR: initiators for continuous activator regeneration.

L: ligand.

M: monomer.

RA: reducing agent.

RAFT: reversible addition-fragmentation chain transfer.

SR&NI: simultaneous reverse and normal initiation.

X: halogen atom.

DETAILED DESCRIPTION OF THE INVENTION

Figure 2:
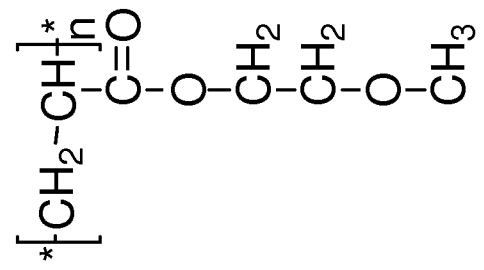
FIG. 2: Structure of poly(2-methoxyethyl acrylate) (PMEA).

Preparation of PMEA coating by SI ATRP such as ARGET SI ATRP or AGET SI ATRP ATRP from one or more surface(s) of a substrate is called Surface-Initiated Atom Transfer Radical Polymerization (SI ATRP). The present invention relates to a method for making a PMEA coating by SI ATRP (see FIGS. 2 to 4) or ARGET SI ATRP (see FIG. 9). In the SI ATRP method 2-methoxyethyl acrylate (MEA) is polymerized from one or more surface(s) and a polymer with the repeating unit shown in FIG. 2 is obtained. Accordingly, MEA is polymerized from one or more surface(s) with initiating groups for ATRP and not in solution. Note that the reaction kinetics for SI ATRP are different from those of ATRP. The invention relates to a PMEA coating obtained by and/or obtainable by SI ATRP such as ARGET SI ATRP or AGET SI ATRP.

The present invention further relates to methods for making a PMEA coating by SI ATRP such as ARGET SI ATRP or AGET SI ATRP.

In one embodiment said SI ATRP such as ARGET SI ATRP or AGET SI ATRP method comprises one or more of the steps of
i) use of initiator groups covalently bound to one or more surface(s) of a substrate
ii) adding one or more catalyst(s), one or more ligand(s), 2-methoxyethyl acrylate and optionally one or more solvents) to a reaction container comprising one or more substrate(s) with one or more surface(s) comprising said initiator groups
iii) allowing the reaction to take place, and optionally
iv) use of one or more reducing agents
thereby making a PMEA coating covalently attached to the surface of the substrate.

In another embodiment said SI ATRP such as ARGET SI ATRP or AGET SI ATRP method comprises one or more of the steps of
i) use of initiator groups covalently bound to one or more surfaces) of a substrate
ii) adding one or more catalyst(s), one or more ligand(s) and optionally one or more solvent(s) to a first reaction container comprising one or more substrate(s) with one or more surface(s) comprising said initiator groups
iii) adding 2-methoxyethyl acrylate and optionally one or more solvent(s) to a second reaction container
iv) optionally remove oxygen from said first reaction container and/or said second reaction container by degassing and/or flushing and/or one or more freeze-pump-thaw cycles,
v) transfer the content of said second container to said first container
vi) allowing the reaction to take place, and optionally
vii) use of one or more reducing agents
thereby making a PMEA coating covalently attached to the surface of the substrate.

In another embodiment said SI ATRP such as ARGET SI ATRP or AGET SI ATRP method comprises one or more of the steps of
i) use of initiator groups covalently bound to one or more surface(s) of a substrate
ii) adding one or more catalyst(s), 2-methoxyethyl acrylate and optionally one or more solvent(s) to a first reaction container comprising one or more substrate(s) with one or more surface(s) comprising said initiator groups
iii) adding one or more ligand(s) and optionally one or more solvent(s) to a second reaction container
iv) optionally remove oxygen from said first reaction container and/or said second reaction container by degassing and/or flushing and/or one or more freeze-pump-thaw cycles,
v) transfer the content of said second container to said first container
vi) allowing the reaction to take place, and optionally
vii) use of one or more reducing agents
thereby making a PMEA coating covalently attached to the surface of the substrate.

In another embodiment said SI ATRP such as ARGET SI ATRP or AGET SI ATRP method comprises one or more of the steps of
i) use of initiator groups covalently bound to one or more surface(s) of a substrate
ii) adding one or more catalyst(s), one or more ligand(s), 2-methoxyethyl acrylate and optionally one or more solvent(s) to a reaction container comprising one or more substrate(s) with one or more surface(s) comprising said initiator groups
iii) optionally remove oxygen from said reaction container by degassing and/or flushing and/or one or more freeze-pump-thaw cycles,
iv) allowing the reaction to take place, and optionally
v) use of one or more reducing agents
thereby making a PMEA coating covalently attached to the surface of the substrate.

In another embodiment said SI ATRP such as ARGET SI ATRP or AGET SI ATRP method comprises one or more of the steps of
i) adding one or more catalyst(s), one or more ligand(s), and optionally one or more solvent(s) to a reaction container comprising one or more substrate(s)
ii) optionally remove oxygen from said reaction container by degassing and/or flushing and/or one or more freeze-pump-thaw cycles,
iii) adding 2-methoxyethyl acrylate and optionally one or more solvent(s) to said reaction container after oxygen has been removed from said reaction container and
iv) allowing the reaction to take place, and optionally
v) use of one or more reducing agents
and thereby preparing a PMEA-coated surface.

In another embodiment said SI ATRP such as ARGET SI ATRP or AGET SI ATRP method comprises one or more of the steps of
i) adding one or more catalyst(s), 2-methoxyethyl acrylate, and optionally one or more solvent(s) to a reaction container comprising one or more substrate(s)
ii) optionally remove oxygen from said reaction container by degassing and/or flushing and/or one or more freeze-pump-thaw cycles,
iii) adding one or more ligand(s) and optionally one or more solvent(s) to said reaction container after oxygen has been removed from said reaction container and
iv) allowing the reaction to take place, and optionally
v) use of one or more reducing agents
and thereby preparing a PMEA-coated surface.

In another embodiment said SI ATRP such as ARGET SI ATRP or AGET SI ATRP method comprises one or more of the steps of
i) adding one or more catalyst(s), 2-methoxyethyl acrylate, one or more ligand(s) and optionally one or more solvent(s) to a reaction container under inert atmosphere such as in a glove box
ii) optionally remove oxygen from said reaction container by degassing and/or flushing and/or one or more freeze-pump-thaw cycles, iii) adding one or more substrates to said reaction container under inert atmosphere
iv) allowing the reaction to take place, and optionally
v) use of one or more reducing agents
and thereby preparing a PMEA-coated surface.

In one embodiment the one or more reducing agents are added to the reaction in excess.

The one or more freeze-pump-thaw cycles used in the preparation of the PMEA coating can be 2, 3, 4, 5, 6, 7, 8 or more than 8 cycles of freeze-pump-thaw cycles.

The reaction for generation of a PMEA coating by SI ATRP such as ARGET SI ATRP or AGET SI ATRP can take place at any temperature such as at from 20° C. to 25° C., for example at from 25° C. to 30° C., such as at from 30° C. to 35° C., for example at from 35° C. to 40° C., such as at from 40° C. to 45° C., for example at from 45° C. to 50° C., such as at from 50° C. to 55° C., for example at from 55° C. to 60° C., such as at from 60° C. to 65° C., for example at from 65° C. to 70° C., such as at from 70° C. to 75° C., for example at from 75° C. to 80° C., such as at from 80° C. to 85° C., for example at from 85° C. to 90° C., such as at from 90° C. to 95° C., for example at from 95° C. to 100° C. or any combination thereof). The reaction can e.g. be performed at 20° C., 25° C., 30° C., 35° C., 40° C., 45° C., 50° C., 55° C., 60° C., 65° C., 70° C., 75° C., 80° C., 90° C., 95° C., or 100° C. or any combination thereof.

The reaction for generation of a PMEA coating by SI ATRP such as ARGET SI ATRP or AGET SI ATRP can take place for any duration of time such as for 1 hour to 2 hours, for example for 2 hours to 3 hours, such as for 3 hours to 4 hours, for example for 4 hours to 5 hours, such as for 5 hours to 6 hours, for example for 6 hours to 7 hours, such as for 7 hours to 8 hours, for example for 8 hours to 9 hours, such as for 9 hours to 10 hours, for example for 10 hours to 11 hours, such as for 11 hours to 12 hours, for example for 12 hours to 13 hours, such as for 13 hours to 14 hours, for example for 14 hours to 15 hours, such as for 15 hours to 16 hours, for example for 16 hours to 17 hours, such as for 17 hours to 18 hours, for example for 18 hours to 19 hours, such as for 19 hours to 20 hours, for example for 20 hours to 21 hours, such as for 21 hours to 22 hours, for example for 22 hours to 23 hours, or such as for 23 hours to 24 hours or any combination thereof. Alternatively, the reaction can take place for less than 24 hours, such as less than 23 hours, for example less than 22 hours, such as less than 21 hours, for example less than 20 hours, such as less than 19 hours, for example less than 18 hours, such as less than 17 hours, for example less than 16 hours, such as less than 15 hours, for example less than 14 hours, such as less than 13 hours, for example less than 12 hours, such as less than 11 hours, for example less than 10 hours, such as less than 9 hours, for example less than 8 hours, such as less than 7 hours, for example less than 6 hours, such as less than 5 hours, for example less than 4 hours, such as less than 3 hours, for example less than 2 hours, such as less than 1 hour, for example less than 50 minutes, such as less than 40 minutes, for example less than 30 minutes, such as less than 20 minutes, for example less than 10 minutes, such as less than 5 minutes, for example less than 1 minute.

The reaction time for generation of a PMEA coating by SI ATRP such as ARGET SI ATRP or AGET SI ATRP determines the length and molecular weight of the polymer chains.

In one embodiment the PMEA coating obtained by the SI ATRP method such as ARGET SI ATRP or AGET SI ATRP comprises chains of PMEA consisting of at least 5 MEA units, such as at least 10 MEA units, for example at least 15 MEA units, such as at least 20 MEA units, for example at least 25 MEA units, such as at least 30 MEA units, for example at least 35 MEA units, such as at least 40 MEA units, for example at least 45 MEA units, such as at least 50 MEA units, for example at least 55 MEA units, such as at least 60 MEA units, for example at least 65 MEA units, such as at least 70 MEA units, for example at least 75 MEA units, such as at least 80 MEA units, for example at least 85 MEA units, such as at least 90 MEA units, for example at least 95 MEA units, such as at least 100 MEA units, for example at least 200 MEA units, such as at least 300 MEA units, for example at least 400 MEA units, such as at least 500 MEA units, for example at least 600 MEA units, such as at least 700 MEA units, for example at least 800 MEA units, such as at least 900 MEA units, for example at least 1000 MEA units.

In another embodiment the PMEA coating obtained by the SI ATRP method such as ARGET SI ATRP or AGET SI ATRP comprises chains of PMEA, wherein at least 50% such as at least 60%, for example at least 70%, such as at least 80%, for example at least 85%, such as at least 90%, for example at least 95%, such as at least 99% of the MEA chains consisting of at least 5 MEA units, such as at least 10 MEA units, for example at least 15 MEA units, such as at least 20 MEA units, for example at least 25 MEA units, such as at least 30 MEA units, for example at least 35 MEA units, such as at least 40 MEA units, for example at least 45 MEA units, such as at least 50 MEA units, for example at least 55 MEA units, such as at least 60 MEA units, for example at least 65 MEA units, such as at least 70 MEA units, for example at least 75 MEA units, such as at least 80 MEA units, for example at least 85 MEA units, such as at least 90 MEA units, for example at least 95 MEA units, such as at least 100 MEA units, for example at least 200 MEA units, such as at least 300 MEA units, for example at least 400 MEA units, such as at least 500 MEA units, for example at least 600 MEA units, such as at least 700 MEA units, for example at least 800 MEA units, such as at least 900 MEA units, for example at least 1000 MEA units.

The PMEA coating can be polymerized from the surface of various substrates which means it will be covalently bound to the surface of said substrate [15].

The one or more catalyst(s) can be selected from the group consisting of CuBr and CuCl. In one preferred embodiment the metal ion in the catalyst is copper. In another embodiment the metal ion can be selected from the group consisting of ruthenium, iron, nickel, palladium, cobalt, rhodium, rhenium, osmium, titanium, lithium, molybdenum, and chromium. Accordingly, ruthenium, iron, nickel, palladium, cobalt, rhodium, rhenium, osmium, titanium, lithium, molybdenum, chromium and copper can work as catalyst in various complexes. In addition, other catalysts in combination with various ligands can be used.

The one or more ligand(s) can be selected from the group consisting of 2,2'-bipyridine, 4,4'-dimethyl-2,2'-bipyridine, 5,5'-dimethyl-2,2'-bipyridine, 5,5'-isopropyl-2,2'-bipyridine, 5,5'-diheptyl-2,2'-bipyridine, 5,5'-ditridecyl-2,2'-bipyridine, 4,4'-di(5-nonyl)-2,2'-bipyridine (dNbpy), 1,10-Phenanthroline (1,10-Phen), 4,7-Diphenyl-1,10-phenanthroline, N,N,N', N'-tetramethylethylenediamine (TMEDA), 2,2':6',2''-terpyridine (tpy), 4,4',4''-tris(5-nonyl)-2,2':6',2''-terpyridine (tNtpy), N,N-bis(2-pyridylmethyl)amine (BPMA), N,N-bis (2-pyridylmethyl)octylamine (BPMOA), N,N-bis(2-pyridylmethyl)propylamine (BPMPrA), N,N-bis(2-pyridylmethyl) octadecylamine (BPMODA), tris[2-aminoethyl]amine (TREN), tris(2-(dimethylamino)ethyl)amine (Me$_6$TREN), tris(2-(diethylamino)ethyl)amine (Et$_6$TREN), tris(2-aminoethyl)-amine-tris[di(2-butoxycarbonylethyl)aminoethyl] amine (BuA$_6$TREN), tris(2-di(methyl acrylate)aminoethyl) amine (MA$_6$TREN), tris(2-di(buthyl acrylate)aminoethyl) amine (BA$_6$TREN), tris[(2-pyridyl)methyl]amine (TPMA), 1,4,8,11-tetraazacyclotetradecane (CYCLAM), 1,4,8,11-tetraaza-1,4,8,11-tetramethylcyclotetradecane (Me$_4$CYCLAM), 4,11-dimethyl-1,4,8,11-tetraazabicyclo[6.6.2]hexadecane referred to as dimethyl cross bridged cyclam (DMCBCy), N,N,N',N'-tetrakis(2-pyridylmethyp-ethylenediamine (TPEN), diethylenetriamine (DETA), triethylenetetramine (TETA), 1,1,4,7,10,10-hexamethyltriethylenetetramine (HMTETA), 1,1,4,7,7-Pentamethyldiethylenetriamine (PMDETA), 1,1,4,7,7-Penta(methyl acrylate)diethylenetriamine (MA$_6$DETA), Glyoxal diimine-type (GlIm-R) ligands, Haddletons ligands (U.S. Pat. No. 6,310,149): N-(n-Pentyl)-2-pyridylmethanimine (n-Pen-1), N-Ethyl-2-pyridylmethanimine (Et-1), N-(n-Propyl)-2-pyridylmethanimine (n-Pr-1), N-(Cyclopropyl)-2-pyridylmethanimine (cyclo-Pr-1), N-(iso-Propyl)-2-pyridylmethanimine (iso-Pr-1), N-(n-Propyl)-2-pyridylmethanimine (n-Pr-3), N-(n-Hexyl)-2-pyridylmethanimine (n-Hex-1), N-(n-Heptyl)-2-pyridylmethanimine (n-Hep-1), N-(n-Octyl)-2-pyridylmethanimine (n-Oct-1), N-(n-Nonyl)-2-pyridylmethanimine (n-Non-1), N-(n-Octadecyl)-2-pyridylmethanimine (n-Octadec-1), n-Propyldiazabutadiene (n-Pr-2), Isopropyldiazabutadiene (iso-Pr-2), Cyclopropyldiazabutadiene (cyclo-Pr-2), 1,4-Dihexyl-2,3-diphenylmethyl-1,4-diaza-1,3-butadiene, and N-(n-Hexyl)-2-pyridylphenylmethanimine.

The one or more solvents can be selected from the group consisting of water, ethanol, methanol, ethanol/water, methanol/water, toluene, propanol, isopropanol, butanol, 1,1,1,3,3,3-hexafluoro-2-propanol or anisole. The ethanol/water or methanol/water can in one embodiment be mixed in the following ratios (volume by volume) 1:1, 1:2, 1:3, 1:4, 1:5, 2:1, 3:1, 4:1, 5:1, (0.1-1):1, 1:(0.1-1) or any other ratio.

The ratio of solvent:MEA can be any ratio (volume by volume) such as (0.1-3):1, for example (0.1-0.2):1, such as (0.2-0.3):1, for example (0.3-0.4):1, such as (0.4-0.5):1, for example (0.5-0.6):1, such as (0.6-0.7):1, for example (0.7-0.8):1, such as (0.8-0.9):1, for example (0.9-1.0):1, such as (1.0-1.1):1, for example (1.1-1.2):1, such as (1.2-1.3):1, for example (1.3-1.4):1, such as (1.4-1.5):1, for example (1.5-1.6):1, such as (1.6-1.7):1, for example (1.7-1.8):1, such as (1.8-1.9):1, for example (1.9-2.0):1, such as (2.0-2.1):1, for example (2.1-2.2):1, such as (2.2-2.3):1, for example (2.3-2.4):1, such as (2.4-2.5):1, for example (2.5-2.6):1, such as (2.6-2.7):1, for example (2.7-2.8):1, such as (2.8-2.9):1, or any combination thereof.

The ratio of MEA:solvent can be any ratio (volume by volume) such as (0.1-3):1, for example (0.1-0.2):1, such as (0.2-0.3):1, for example (0.3-0.4):1, such as (0.4-0.5):1, for example (0.5-0.6):1, such as (0.6-0.7):1, for example (0.7-0.8):1, such as (0.8-0.9):1, for example (0.9-1.0):1, such as (1.0-1.1):1, for example (1.1-1.2):1, such as (1.2-1.3):1, for example (1.3-1.4):1, such as (1.4-1.5):1, for example (1.5-1.6):1, such as (1.6-1.7):1, for example (1.7-1.8):1, such as (1.8-1.9):1, for example (1.9-2.0):1, such as (2.0-2.1):1, for example (2.1-2.2):1, such as (2.2-2.3):1, for example (2.3-2.4):1, such as (2.4-2.5):1, for example (2.5-2.6):1, such as (2.6-2.7):1, for example (2.7-2.8):1, such as (2.8-2.9):1, or any combination thereof.

In another embodiment the ratio of solvent:MEA is 1:1 (volume by volume).

The ratio of MEA:catalyst:ligand can be any ratio (mole by mole) such as (30-1000):1:(1-3), for example (30-50):1:(1-3), such as (50-100):1:(1-3), for example (100-150):1:(1-3), such as (150-200):1:(1-3), for example (200-250):1:(1-3), such as (250-300):1:(1-3), for example (300-350):1:(1-3), such as (350-400):1:(1-3), for example (400-450):1:(1-3), such as (450-500):1:(1-3), for example (500-550):1:(1-3), such as (550-600):1:(1-3), for example (600-650):1:(1-3), such as (650-700):1:(1-3), for example (700-750):1:(1-3), such as (750-800):1:(1-3), for example (800-850):1:(1-3), such as (850-900):1:(1-3), for example (900-950):1:(1-3), such as (950-1000):1:(1-3), for example (30-50):1:(1-2), such as (50-100):1:(1-2), for example (100-150):1:(1-2), such as (150-200):1:(1-2), for example (200-250):1:(1-2), such as (250-300):1:(1-2), for example (300-350):1:(1-2), such as (350-400):1:(1-2), for example (400-450):1:(1-2), such as (450-500):1:(1-2), for example (500-550):1:(1-2), such as (550-600):1:(1-2), for example (600-650):1:(1-2), such as (650-700):1:(1-2), for example (700-750):1:(1-2), such as (750-800):1:(1-2), for example (800-850):1:(1-2), such as (850-900):1:(1-2), for example (900-950):1:(1-2), such as (950-1000):1:(1-2), for example (30-50):1:(2-3), such as (50-100):1:(2-3), for example (100-150):1:(2-3), such as (150-200):1:(2-3), for example (200-250):1:(2-3), such as (250-300):1:(2-3), for example (300-350):1:(2-3), such as (350-400):1:(2-3), for example (400-450):1:(2-3), such as (450-500):1:(2-3), for example (500-550):1:(2-3), such as (550-600):1:(2-3), for example (600-650):1:(2-3), such as (650-700):1:(2-3), for example (700-750):1:(2-3), such as (750-800):1:(2-3), for example (800-850):1:(2-3), such as (850-900):1:(2-3), for example (900-950):1:(2-3), such as (950-1000):1:(2-3), or any combination thereof.

In another embodiment the ratio of MEA:catalyst:ligand (equivalents; mole by mole) is (1-2000):1:(0.1-50).

None limiting examples of substrates are listed herein below.

Polymeric or organic substrates: Poly(ether ether ketone) (PEEK), Polypropylene (PP), Polyethylene (PE) (including linear low density polyethylene (LLDPE), low density polyethylene (LOPE) high density polyethylene (HDPE), ultra high molecular weight polyethylene (UHMWPE), and crass-linked polyethylene (PEX)), Polyethylene terephthalate) (PET), poly(propylene terephthalate (PPT), PPT/PET copolyester, Polybutylene terephthalate (PBT), Poly(vinyl chloride) (PVC), Polyamide/nylon (PA), Polycarbonate (PC), Cyclic olefin copolymer (COC), Filter paper, Cotton, Cellulose, Poly(4-vinylbenzyl chloride) (PVBC), Poly(vinylidene fluoride) (PVDF), Polystyrene (PS), Toyopearl®, Hydrogels, Polyimide (PI), 1,2-Polybutadiene (PB), Liquid silicon rubber (LSR), poly(dimethylsiloxane) (PDMS), fluoropolymers- and copolymers (e.g. poly(tetrafluoroethylene) (PTFE), Perfluoroethylene propylene copolymer (FEP), Ethylene tetrafluoroethylene copolymer (ETFE), Polyvinyl fluoride (PVF), Polyvinylidene fluoride (PVDF), Polychlorotrifluoroethylene (PCTFE)), poly(methyl methacrylate) (PMMA), Acrylonitrile butadiene styrene (ABS), styrene acrylonitrile (SAN), polyacrylonitrile (PAN), Polymethylpentene (TPX), Polyoxymethylene (POM), Polysulfone (PSU), polyetherimide (PEI), polyphenylene oxide (PPO), polyethersulfone (PES), Polyphenylene sulfide (PPS), Polyamideimide (PAl), Liquid crystal polymer (LCP), Epoxy, Polyurethane (PU), Thermoplastic elastomer (TPE), natural or synthetic rubber, polybutadiene (PB) etc. Natural synthetic rubber comprises polyisobutylene (PIB), polyisoprene, poly (ethylene-co-propylene), Kraton polymers: Poly(styrene-b-butadiene-b-styrene) (SBS), poly(styrene-b-isoprene-b-styrene) (SIS), poly(styrene-b-(ethylene/butylene)-b-styrene) (SEBS), poly(styrene-b-(ethylene/propylene)-b-styrene) (SEPS).

Metallic or inorganic substrates: Titanium, gold, glass, silicon, geranium, quartz, silicon oxide, silica, stainless steel, diamond, magnetic nanoparticles (e.g. Fe$_3$O$_4$) etc.

Other: Nanoporous materials, Membranes, Mesostructured cellular foam (MCF), and singlewall or multiwall Carbon Nanotubes (SWCNT, MWCNT).

In principle Surface-Initiated Atom Transfer Radical Polymerization (SI-ATRP) can be performed on all materials provided that they can be coupled to an initiator for ATRP [15]. Some materials have functional groups which can be used directly for the coupling whereas others will need to be activated before the coupling reaction to the initiator can take place [14, 15, 16, 17].

Initiation Systems

A standard ATRP initiating system is described in the background for the invention. Reverse ATRP involves in one embodiment in situ formation of $Cu^I$ from standard free radical initiators (e.g. AIBN) and $Cu^{II}$ salt which makes it less prone to oxidation problems and more useful for commercial applications. The transferable halogen atom is part of the copper salt in reverse ATRP i.e. ATRP initiator is not added; therefore, the catalyst concentration must be comparable to the concentration of the initiator. For the technique SR&NI ATRP a dual initiating system is present consisting of standard free radical initiators and initiators with a transferable atom or group. The radicals formed by AIBN are deactivated by an oxidatively stable $Cu^{II}$ salt in that way $Cu^I$ and some halogenated chains are generated. Thus $Cu^I$ can reactivate the alkyl halide initiators and mediate normal ATRP. The ICAR ATRP method differs from SR&NI by use of a large excess of free radical initiator to catalyst. The radicals are slowly formed during the reaction and mechanistic studies have shown resemblance between the kinetics of ICAR and RAFT. AGET ATRP utilizes reducing agents which are unable to initiate new chains. The reducing agent reacts in one embodiment with the $Cu^{II}$ complex and forms the $Cu^I$ ATRP activator. $Cu^0$, $tin^{II}$ 2-ethylhexanoate, ascorbic acid, and triethylamine have been reported as reducing agents for AGET ATRP. In ARGET ATRP the $Cu^{II}$ is continuously reduced to $Cu^I$ as a large enough excess of reducing agent to copper is applied. This makes it possible to lower the concentration of catalyst to initiator significantly. Good control was obtained with 50 ppm of copper for ARGET ATRP of acrylate and 10 ppm of copper for styrene polymerization. In addition to the reducing agents for AGET ATRP a number of organic derivatives of hydrazine, phenol, sugar, and ascorbic acid as well as inorganic species such as $Sn^{II}$ and $Cu^0$ can be used for ARGET ATRP[18]. Table A herein below gives an overview of the ratios and reagents which can be applied in the techniques.

TABLE A

Examples of typical ratios used for the different ATRP initiation systems [18].

| ATRP method | MIR-X/$Cu^I$X/$Cu^{II}$X | L (ligand) | RA (reducing agent) | AIBN |
|---|---|---|---|---|
| Normal | 200/1/1/— | 1 | — | — |
| Reverse | 200/—/—/1 | 1 | — | 0.5 |
| SR&NI | 200/1/—/0.2 | 0.2 | — | 0.1 |
| ICAR | 200/1/—/<0.01 | 0.01 | — | <0.1 |
| AGET | 200/1/—/0.2 | 0.2 | 0.18 | — |
| ARGET | 200/1/—/<0.01 | 0.1 | <0.1 | — |

In one embodiment the present invention relates to ARGET ATRP wherein low concentration of catalyst to initiator is used.

The PMEA Coating

The coating of the present invention is a biocompatible coating e.g. compatible with biological material such as protein, peptide, body liquids such as blood, skin, tissue such as fatty tissue.

Advantages of the covalently linked PMEA coating of the present invention compared to a traditional physically adhered PMEA coating are e.g. the following characteristics of the present coating:
  prevention or inhibition of bacterial growth
  bacteria repellent activity
  Improved long-term stability
  Change of friction and wear The above mentioned inhibition of bacterial growth can be an inhibition of the bacterial growth with more than 50%, such as more than 60%, for example more than 70%, such as more than 80%, for example more than 90%, such as more than 95% or such as more than 99% compared to a surfaced that is not coated with PMEA.

Another advantage is that there will be less leakage of the PMEA from a covalently bound PMEA coating than from a physically adhered PMEA coating. This can be an advantage e.g. for coatings on an implantable device. In one embodiment e.g. under moderate conditions there will be no leakage from the covalently bound PMEA coating. In another embodiment there will be less than 10% leakage, such as less than 9%, for example less than 8%, such as less than 7%, for example less than 6%, such as less than 5%, for example less than 4%, such as less than 3%, for example less than 2%, such as less than 1%, for example less than 0.5%, such as less than 0.1%, for example less than 0.01% leakage.

Importantly, a PMEA coating which is covalently bound to one or more surface(s) has an improved stability compared to a physically adhered PMEA coating. This improvement is of crucial importance for applications within the field of medical devices. Furthermore, the SI ATRP such as ARGET SI ATRP or AGET SI ATRP methods are more specific and effective compared to the ATRP method for generation of a PMEA coating.

In one embodiment the PMEA coating prepared by SI ATRP such as ARGET SI ATRP or AGET SI ATRP will lower the water contact angle of the substrate.

Use of the PMEA Coating

The PMEA coating can be used in the area of biocompatible surface, i. e. those materials that are used in contact with living or dead tissue and biological fluids for prosthetic, therapeutic, diagnostics, storage or other applications. Many conventional biocompatible surfaces lack the ability to properly interact with or support biological matter coming into contact with said biocompatible surface leading to undesired biological responses.

The PMEA coating can be used to produce a biocompatible surface e.g. for contact with e.g. one or more subject matters selected from the group consisting of one or more protein(s), one or more peptide(s), one or more liquid(s) comprising one or more protein(s), one or more liquid(s) comprising one or more peptide(s), one or more pharmaceuticals, one or more body liquids, one or more tissues, and meat. The body liquids can in one embodiment be selected from the group consisting of blood, serum, blood plasma, amniotic fluid, aqueous humour, cerumen, Cowper's fluid or pre-ejaculatory fluid, chyme, female ejaculate, interstitial fluid, lymph, breast milk, mucus (including nasal drainage and phlegm), pleural fluid, pus, saliva, sebum (skin oil), semen, sweat, tears, urine, vaginal secretion and vomit. In one preferred embodiment the PMEA coating can be used as a blood-contacting surface e.g. for a medical device.

The PMEA coated biocompatible surfaces of substrates may thus be used as containers, cell-culture dishes, bioreactors, implants, biohybrid organs such as pacemakers, bioartificial pancreas, liver or kidney, and the like.

The invention also pertains to the use of the PMEA coating in a method of controlling cellular growth and/or cellular proliferation and/or cellular differentiation in vivo, or use of the material in a method of separating and/or isolating biological material in vivo, or use of the material in a method of controlling cellular growth and/or cellular proliferation and/or cellular differentiation ex vivo, or use of the material in a method of separating and/or isolating biological material ex vivo, or use of the material in a method of producing a biohybrid organ ex vivo, and the use of the material in the manufacture of an implantable organ or part thereof.

The PMEA coating according to the invention may also be used as a carrier for a pharmaceutically active ingredient or a pharmaceutical formulation or composition.

The invention also pertains to the following methods:

Method of therapy carried out on the human or animal body, said method comprising the step of contacting said body with the PMEA coating according to the present invention.

Method of surgery carried out on the human or animal body, said method comprising the step of contacting said body with the PMEA coating according to the invention.

Method of diagnosis carried out on the human or animal body, said method comprising the steps of contacting said body with the PMEA coating according to the present invention, and detecting a signal generated directly or indirectly by said PMEA coating.

A Container

In one embodiment the PMEA coating according to the present invention can be used for coating of a container. Said container can be used for storage of e.g. one or more subject matters selected from the group consisting of one or more protein(s), one or more peptide(s), one or more liquid(s) comprising one or more protein(s), one or more liquid(s) comprising one or more peptide(s), one or more enzymes, one or more pharmaceuticals, one or more body liquids, one or more tissues, meat, cells including bacteria and mammalian cells such as human cells.

The container coated with the covalently bound PMEA coating can in one embodiment be used for storage of one or more body liquids. The body liquids can in one embodiment be selected from the group consisting of blood, serum, blood plasma, amniotic fluid, aqueous humour, cerumen, Cowper's fluid or pre-ejaculatory fluid, chyme, female ejaculate, interstitial fluid, lymph, breast milk, mucus (including nasal drainage and phlegm), pleural fluid, pus, saliva, sebum (skin oil), semen, sweat, tears, urine, vaginal secretion and vomit.

In one embodiment the container coated with the PMEA coating of the present invention can be used for storage to prevent or limit bacterial growth inside said container. Accordingly, the coating can be used to inhibit and/or prevent non-specific fouling.

The PMEA coating disclosed by the present invention can be used for coating of a container such as any container (with or without a lid) with a void cavity suitable for storage such as a bottle, flask, bag, blood bag, pot, tub, dish, tray, bowl, basin, pill bottle, medicine bottle, ampoule, flagon, syringe, needle, tube, cell culture dish or flask or tissue culture dish or flask, bioreactor, pipette tip, or Pasteur pipette. The lid can also be coated if needed.

In one embodiment the invention relates to use of the PMEA coating for coating of a container that can e.g. be used for sampling in a laboratory during diagnostics such as a test tube, PCR tube, an eppendorf tube, a blood sample glass, or a conical test tube, tissue culture dish or flask, cell culture dish or flask, slides for microscopic inspection, chamber slide, biopsy needle.

A Medical Device Including Implantable Devices

The PMEA coating disclosed by the present invention can be used for coating of a medical device such as an implantable device such as a hip replacement or a stent. The medical device can be selected from the group consisting of a blood filter, a blood storage bag, a blood circuit, an indwelling needle, a catheter, a pump, an infusion set, a guide wire, a stent, an oxygenator, a dialyzer and an adhesive for tissues.

The medical device can further be an apparatus used for blood collection such as a blood collection equipment consisting of a plastic hub, a hypodermic needle, and a vacuum tube. In one embodiment the blood collection equipment is an evacuated tube system, such as the RD Vacutainer system. Alternatively, the blood collection equipment comprises a syringe with a butterfly needle, which is a plastic catheter attached to a short needle. In another embodiment the blood collection equipment comprises one or more Vacuum tubes.

The medical device can further be selected from the group consisting of, blood collection tubes, vacuum blood collection tubes, vacuum tubes, negative pressure blood taking tube, capillary blood collection tube, blood transfusion equipment, blood sample equipment, blood transfusion set, infusion set, blood collection needle, serum tube, plasma tube, blood tube, bidirectional blood needle, cardiopulmonary bypass circuits and oxygenators.

The medical device can further be a drug delivery device. Drug delivery devices are specialized tools for the delivery of a drug or therapeutic agent via a specific route of administration. Such devices are used as part of one or more medical treatments.

Drug delivery devices include, but are not limited to, the following:

An autoinjector such as a dual-chamber autoinjector which is a medical device designed to deliver a single dose of a particular (e.g. life-saving) drug. Most autoinjectors are spring-loaded syringes.

A drug-eluting stent (DES) which is a coronary stent (a scaffold) placed into narrowed, diseased coronary arteries that slowly releases a drug e.g. to block cell proliferation.

A Dry powder inhaler (DPI) which is a device that delivers medication to the lungs in the form of a dry powder. DPIs can be used to treat respiratory diseases such as asthma, bronchitis, emphysema, COPD and diabetes mellitus.

Inhaler, Metered-dose inhaler or Respimat a needle-based injector, e.g. computer-controlled, battery-powered medical drug delivery device e.g. for delivery of the recombinant human growth hormone somatropin.

a needle-free injector drug delivery device which, instead of accelerating a liquid jet across the skin like other needle-free injectors, uses a solid dose. The dose itself is the delivery vehicle.

a pen injector using short needles to deliver precise doses of e.g. insulin.

An infusion pump infuses fluids, medication or nutrients into a patient's circulatory system. It is generally used intravenously, although subcutaneous, arterial and epidural infusions are occasionally used.

Intraject is a needle-free injector medical device (drug delivery device) which accelerates a liquid jet across the skin to deliver the dose. It is a needle-free, prefilled, single-use, disposable, subcutaneous drug injection system.

A jet injector is a type of medical injecting syringe that uses a high-pressure narrow jet of the injection liquid instead of a hypodermic needle to penetrate the epidermis, the purpose being to reduce the pain associated with needle injection.

The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device itself, such as a stent, can also be made from the described inventive PMEA coating.

Other examples of implantable devices include pacemaker, hip replacement, stent, brain implant, breast implant, buttock implant, cochlear implant, dental implant, extraocular implant, Harrington implant, Microchip implant, Retinal implant, Subdermal implant, and transdermal implant.

The medical device can also be one or more prostheses. Prostheses can be used to replace body parts lost by injury (traumatic) or missing from birth (congenital) or to supplement defective body parts. Inside the body, artificial heart valves are in common use with artificial hearts and lungs seeing less common use but under active technology development. Other medical devices and aids that can be considered prosthetics include artificial eyes, palatal obturator, gastric bands, dentures, artificial limbs, artificial organs, artificial knee, Lower Extremity Prosthetics, Hip disarticulations prosthetics, Knee disarticulations prosthetics, Symes prosthetics.

The PMEA coating according to the invention can also be used for coating of neuromotor prostheses or neurocognitive prostheses such as implantable neurocognitive brain-computer interfaces for treat of a condition and/or disease such as stroke, traumatic brain injury, cerebral palsy, autism, and Alzheimer's disease.

The PMEA coating can also be used for coating of biosensors. Biosensors detect signals from the users nervous or muscular systems. Examples of biosensors include wires that detect electrical activity on the skin, needle electrodes implanted in muscle, or solid-state electrode arrays with nerves growing through them. One type of these biosensors are employed in Myoelectric prosthesis.

In one embodiment the PMEA coating can be used for prevention and/or inhibition of infection associated with a medical device and/or implant.

A Tubing Device

The PMEA coating according to the present invention can be used for coating of a tube. The tubes can be any type of tube such as a tube made of glass or plastic. The tube can be used for transport of one or more subject matters selected from the group consisting of one or more protein(s), one or more peptide(s), one or more liquid(s) comprising one or more protein(s), one or more liquid(s) comprising one or more peptide(s), one or more enzymes, one or more pharmaceuticals, one or more body liquids such as blood, blood plasma or serum, one or more tissues, meat, cells including bacteria and mammalian cells such as human cells.

The tube can e.g. be a tube of an infusion set or blood transfusion equipment. The tube can also be part of laboratory equipment such as a device for chromatographic separation.

The PMEA coating according to the present invention can be used for coating of a catheter.

The catheter is in one embodiment a tube that can be inserted into a body cavity, duct, or vessel. The catheter thereby allow drainage, injection of fluids, or access by surgical instruments. In most uses, the catheter is a thin, flexible tube ("soft" catheter), though in some uses, it is a larger, solid ("hard") catheter. The catheter can be left inside the body, either temporarily or permanently (referred to as an indwelling catheter). A permanently inserted catheter may be referred to as a permcath.

Placement of the PMEA coated catheter into a particular part of the body can e.g. allow:
- draining urine from the urinary bladder as in urinary catheterization, e.g., the Foley catheter or even when the urethra is damaged as in suprapubic catheterisation.
- drainage of urine from the kidney by percutaneous nephrostomy
- drainage of fluid collections, e.g. an abdominal abscess
- administration of intravenous fluids, medication or parenteral nutrition with a peripheral venous catheter
- angioplasty, angiography, balloon septostomy, balloon sinuplasty, catheter ablation
- direct measurement of blood pressure in an artery or vein
- direct measurement of intracranial pressure
- administration of anaesthetic medication into the epidural space, the subarachnoid space, or around a major nerve bundle such as the brachial plexus
- subcutaneous administration of insulin or other medications e.g. with the use of an infusion set and/or insulin pump
- A central venous catheter is a conduit for giving drugs or fluids into a large-bore catheter positioned either in a vein near the heart or just inside the atrium.
- A Swan-Ganz catheter is a special type of catheter placed into the pulmonary artery for measuring pressures in the heart.
- An umbilical line is a catheter used in Neonatal Intensive Care Units (NICU) providing quick access to the central circulation of premature infants.
- A Touhy burst adapter is a medical device used for attaching catheters to various other devices.
- A Quinton catheter is a double or triple lumen, external catheter used for hemodialysis.

A Separation Media

The PMEA coating according to the present invention can be used for preparation of separation media such as a membrane or filter for selective separation or purification of specific biological components like proteins, peptides and cells from biological fluids. Such separation media can be any which is suited for immobilisation, separation etc. such as filters, membranes, ultrafiltration membranes, nanoporous membranes, anti-fouling membranes, Silicone-Based Membrane, nanofiltration membranes, blood purification membrane, Membranes for Reverse Osmosis Desalinization, Reverse osmosis membrane, Hollow Fiber Membranes, Ion-exchange membrane, beads, fibres, webs, sinters or sieves The separation media can be a filter medium for selectively removing components from biological fluids e.g. leucocytes from blood and blood products.

The invention will e.g. enable the use of improved membranes for ensuring spatial separation of e.g. xenogenic and/or allogenic cells from the host immune system.

Modifying membranes with the PMEA coating according to the present invention can reduce the amount of adsorption of biological material such as proteins, peptides or cells on the plane of the membrane and at the same time improve the conformational/functional state/form of adsorbed proteins, peptides or cells.

The coating according to the present invention can further be used on anti-fouling membranes e.g. in sensors, pumps, bioreactors, desalination, dialyses, blood purification etc.

A Film

The PMEA coating according to the present invention can also be used for coating of one or more films such as polymer film(s), single or multiple layer films, e.g. for food and/or feed packaging, pharmaceutical packaging, blood bags etc.

The present invention is in one embodiment characterised by the items herein below. Items:

1. A polymer coating comprising or consisting of polymer chains comprising or consisting of repeating units of 2-methoxyethyl acrylate, wherein said polymer chains are covalently bound to one or more surface(s) of one or more substrate(s).
2. The polymer coating according to item 1, wherein the polymer coating is obtained or obtainable by SI ATRP, reverse ATRP, SR and NI ATRP, ICAR ATRP, AGET ATRP and/or ARGET ATRP.
3. The polymer coating according to item 1, wherein said polymer chains comprises chains of PMEA consisting of at least 5 MEA units, such as at least 10 MEA units, for example at least 15 MEA units, such as at least 20 MEA units, for example at least 25 MEA units, such as at least 30 MEA units, for example at least 35 MEA units, such as at least 40 MEA units, for example at least 45 MEA units, such as at least 50 MEA units, for example at least 55 MEA units, such as at least 60 MEA units, for example at least 65 MEA units, such as at least 70 MEA units, for example at least 75 MEA units, such as at least 80 MEA units, for example at least 85 MEA units, such as at least 90 MEA units, for example at least 95 MEA units, such as at least 100 MEA units, for example at least 200 MEA units, such as at least 300 MEA units, for example at least 400 MEA units, such as at least 500 MEA units, for example at least 600 MEA units, such as at least 700 MEA units, for example at least 800 MEA units, such as at least 900 MEA units, for example at least 1000 MEA units.
4. The polymer coating according to item 1, wherein said polymer chains comprises chains of PMEA, wherein at least 50% such as at least 60%, for example at least 70%, such as at least 80%, for example at least 85%, such as at least 90%, for example at least 95%, such as at least 99% of the MEA chains consisting of at least 5 MEA units, such as at least 10 MEA units, for example at least 15 MEA units, such as at least 20 MEA units, for example at least 25 MEA units, such as at least 30 MEA units, for example at least 35 MEA units, such as at least 40 MEA units, for example at least 45 MEA units, such as at least 50 MEA units, for example at least 55 MEA units, such as at least 60 MEA units, for example at least 65 MEA units, such as at least 70 MEA units, for example at least 75 MEA units, such as at least 80 MEA units, for example at least 85 MEA units, such as at least 90 MEA units, for example at least 95 MEA units, such as at least 100 MEA units, for example at least 200 MEA units, such as at least 300 MEA units, for example at least 400 MEA units, such as at least 500 MEA units, for example at least 600 MEA units, such as at least 700 MEA units, for example at least 800 MEA units, such as at least 900 MEA units, for example at least 1000 MEA units.
5. A device comprising one or more surface(s) covalently bound to the polymer coating according any of to items 1 to 4.
6. The device according to item 5, wherein said device is a container.
7. The device according to item 5, wherein said device is an implantable device.
8. The device according to item 5, wherein said device is a tubing device.
9. The device according to item 5, wherein said device is a membrane.
10. The device according to item 5, wherein said device is a film.
11. The device according to item 5, wherein said device is a medical device.
12. The device according to item 5, wherein said device can be selected from the group consisting of cell culture dishes or flasks, bioreactors, syringe, needle, biopsy needle, pipette tip, test tube, slide for microscopic inspection, medicine bottle or ampoule, bag, pouch, implantable device, stent, blood filter, blood storage bag, a blood sample glass or tube, blood filter, a blood circuit, infusion set, pump, a catheter, a pump, an oxygenator, prostheses, and biosensors.
13. A method for making the polymer coating according any of to items 1 to 4.
14. The method according to item 13, wherein the method comprises SI ATRP such as ARGET SI ATRP or AGET SI ATRP.
15. The method according to item 13, wherein MEA is polymerized from one or more surface(s) of one or more substrate(s).
16. The method according to item 13, wherein the method comprises one or more of the steps of
i) use of initiator groups covalently bound to one or more surface(s) of a substrate
ii) adding one or more catalyst(s), one or more ligand(s), 2-methoxyethyl acrylate and optionally one or more solvent(s) to a reaction container comprising one or more substrate(s) with one or more surface(s) comprising said initiator groups
iii) allowing the reaction to take place, and optionally
iv) use of one or more reducing agents
thereby making the polymer coating according to item 1.
17. The method according to item 13, wherein the method comprises one or more of the steps of
i) use of initiator groups covalently bound to one or more surface(s) of a substrate
ii) adding one or more catalyst(s), one or more ligand(s) and optionally one or more solvent(s) to a first reaction container comprising one or more substrate(s) with one or more surface(s) comprising said initiator groups
iii) adding 2-methoxyethyl acrylate and optionally one or more solvent(s) to a second reaction container iv) optionally remove oxygen from said first reaction container and/or said second reaction container by degassing and/or flushing and/or one or more freeze-pump-thaw cycles,
v) transfer the content of said second container to said first container
vi) allowing the reaction to take place, and optionally
vii) use of one or more reducing agents
thereby making a PMEA coating covalently attached to the surface of the substrate.

18. The method according to item 13, wherein the method comprises one or more of the steps of
i) use of initiator groups covalently bound to one or more surface(s) of a substrate
ii) adding one or more catalyst(s), 2-methoxyethyl acrylate and optionally one or more solvent(s) to a first reaction container comprising one or more substrate(s) with one or more surface(s) comprising said initiator groups
iii) adding one or more ligand(s) and optionally one or more solvent(s) to a second reaction container
iv) optionally remove oxygen from said first reaction container and/or said second reaction container by degassing and/or flushing and/or one or more freeze-pump-thaw cycles,
v) transfer the content of said second container to said first container
vi) allowing the reaction to take place, and optionally
vii) use of one or more reducing agents
thereby making a PMEA coating covalently attached to the surface of the substrate.

19. The method according to item 13, wherein the method comprises one or more of the steps of
i) use of initiator groups covalently bound to one or more surface(s) of a substrate
ii) adding one or more catalyst(s), one or more ligand(s), 2-methoxyethyl acrylate and optionally one or more solvent(s) to a reaction container comprising one or more substrate(s) with one or more surface(s) comprising said initiator groups
iii) optionally remove oxygen from said reaction container by degassing and/or flushing and/or one or more freeze-pump-thaw cycles,
iv) allowing the reaction to take place, and optionally
v) use of one or more reducing agents
thereby making a PMEA coating covalently attached to the surface of the substrate.

20. The method according to item 13, wherein the method comprises one or more of the steps of
i) adding one or more catalyst(s), one or more ligand(s), and optionally one or more solvent(s) to a reaction container comprising one or more substrate(s)
ii) optionally remove oxygen from said reaction container by degassing and/or flushing and/or one or more freeze-pump-thaw cycles,
iii) adding 2-methoxyethyl acrylate and optionally one or more solvent(s) to said reaction container after oxygen has been removed from said reaction container and
iv) allowing the reaction to take place, and optionally
v) use of one or more reducing agents
and thereby preparing a PMEA-coated surface.

21. The method according to item 13, wherein the method comprises one or more of the steps of
i) adding one or more catalyst(s), 2-methoxyethyl acrylate, and optionally one or more solvent(s) to a reaction container comprising one or more substrate(s)
ii) optionally remove oxygen from said reaction container by degassing and/or flushing and/or one or more freeze-pump-thaw cycles,
iii) adding one or more ligand(s) and optionally one or more solvent(s) to said reaction container after oxygen has been removed from said reaction container and
iv) allowing the reaction to take place, and optionally
v) use of one or more reducing agents
and thereby preparing a PMEA-coated surface.

22. The method according to item 13, wherein the method comprises one or more of the steps of
i) adding one or more catalyst(s), 2-methoxyethyl acrylate, one or more ligand(s) and optionally one or more solvent(s) to a reaction container under inert atmosphere such as in a glove box
ii) optionally remove oxygen from said reaction container by degassing and/or flushing and/or one or more freeze-pump-thaw cycles,
iii) adding one or more substrates to said reaction container under inert atmosphere
iv) allowing the reaction to take place, and optionally
v) use of one or more reducing agents
and thereby preparing a PMEA-coated surface.

23. The method according to any of items 13 to 22, wherein the reaction is allowed to take place at a temperature between 20° C. and 100° C.

24. The method according to any of items 13 to 23, wherein the reaction is allowed to take place at a temperature interval between 20° C. and 100° C. such as at from 20° C. to 25° C., for example at from 25° C. to 30° C., such as at from 30° C. to 35° C., for example at from 35° C. to 40° C., such as at from 40° C. to 45° C., for example at from 45° C. to 50° C., such as at from 50° C. to 55° C., for example at from 55° C. to 60° C., such as at from 60° C. to 65° C., for example at from 65° C. to 70° C., such as at from 70° C. to 75° C., for example at from 75° C. to 80° C., such as at from 80° C. to 85° C., for example at from 85° C. to 90° C., such as at from 90° C. to 95° C., for example at from 95° C. to 100° C. or any combination thereof). The reaction can e.g. be performed at 20° C., 25° C., 30° C., 35° C., 40° C., 45° C., 50° C., 55° C., 60° C., 65° C., 70° C., 75° C., 80° C., 90° C., 95° C., or 100° C., or any combination thereof.

25. The method according to any of items 13 to 24, wherein the reaction is allowed to take place for any duration of time between 1 hour and 24 hours such as for 1 hour to 2 hours, for example for 2 hours to 3 hours, such as for 3 hours to 4 hours, for example for 4 hours to 5 hours, such as for 5 hours to 6 hours, for example for 6 hours to 7 hours, such as for 7 hours to 8 hours, for example for 8 hours to 9 hours, such as for 9 hours to 10 hours, for example for 10 hours to 11 hours, such as for 11 hours to 12 hours, for example for 12 hours to 13 hours, such as for 13 hours to 14 hours, for example for 14 hours to 15 hours, such as for 15 hours to 16 hours, for example for 16 hours to 17 hours, such as for 17 hours to 18 hours, for example for 18 hours to 19 hours, such as for 19 hours to 20 hours, for example for 20 hours to 21 hours, such as for 21 hours to 22 hours, for example for 22 hours to 23 hours, or such as for 23 hours to 24 hours or any combination thereof.

26. The method according to any of items 13 to 25, wherein the reaction is allowed to take place for any duration of time for example less than 24 hours, such as less than 23 hours, for example less than 22 hours, such as less than 21 hours, for example less than 20 hours, such as less than 19 hours, for example less than 18 hours, such as less than 17 hours, for example less than 16 hours, such as less than 15 hours, for example less than 14 hours, such as less than 13 hours, for example less than 12 hours, such as less than 11 hours, for example less than 10 hours, such as less than 9 hours, for example less than 8 hours, such as less than 7 hours, for example less than 6 hours, such as less than 5 hours, for example less than 4 hours, such as less than 3 hours, for example less than 2 hours, such as less than 1 hour, for example less than 50 minutes, such as less than 40 minutes, for example less than 30 minutes, such as less than 20 minutes, for example less than 10 minutes, such as less than 5 minutes, for example less than 1 minute.

27. The method according to any of items 13 to 26, wherein the one or more catalyst(s) is CuBr.
28. The method according to any of items 13 to 27, wherein the one or more catalyst(s) is CuCl.
29. The method according to any of items 13 to 28, wherein the one or more catalyst(s) is a catalyst wherein the metal ion is copper.
30. The method according to any of items 13 to 29, wherein the one or more catalyst(s) is a catalyst wherein the metal ion is selected from the group consisting of ruthenium, iron, nickel, palladium, cobalt, rhodium, rhenium, osmium, titanium, lithium, molybdenum, and chromium.
31. The method according to any of items 13 to 30, wherein the one or more catalyst(s) is $CuBr_2$ and/or $CuCl_2$.
32. The method according to any of items 13 to 31, wherein the one or more catalyst(s) is $CuBr_2$ and/or $CuCl_2$ and wherein one or more reducing agents are used.
33. The method according to items 32, wherein the one or more reducing agents can be selected from the group consisting of $tin^{II}$ 2-ethylhexanoate, ascorbic acid, triethylamine, a number of organic derivatives of hydrazine, phenol, sugar as well as inorganic species such as $Sn^{II}$ and $Cu^0$.
34. The method according to any of items 13 to 33, wherein the one or more ligand(s) can be selected from the group consisting of 2,2'-bipyridine, 4,4'-dimethyl-2,2'-bipyridine, 5,5'-dimethyl-2,2'-bipyridine, 5,5'-isopropyl-2,2'-bipyridine, 5,5'-diheptyl-2,2'-bipyridine, 5,5'-ditridecyl-2,2'-bipyridine, 4,4'-di(5-nonyl)-2,2'-bipyridine (dNbpy), 1,10-Phenanthroline (1,10-Phen), 4,7-Diphenyl-1,10-phenanthroline, N,N,N',N'-tetramethylethylenediamine (TMEDA), 2,2':6',2"-terpyridine (tpy), 4,4',4"-tris(5-nonyl)-2,2':6',2"-terpyridine (tNtpy), N,N-bis(2-pyridylmethyl)amine (BPMA), N,N-bis(2-pyridylmethyl)octylamine (BPMOA), N,N-bis(2-pyridylmethyl)propylamine (BPMPrA), N,N-bis(2-pyridylmethyl)octadecylamine (BPMODA), tris[2-aminoethyl]amine (TREN), tris(2-(dimethylamino)ethyl)amine ($Me_6TREN$), tris(2-(diethylamino)ethyl)amine ($Et_6TREN$), tris(2-aminoethyl)-amine-tris[di(2-butoxycarbonylethyl)aminoethyl]amine ($BuA_6TREN$), tris(2-di(methyl acrylate)aminoethyl)amine ($MA_6TREN$), tris(2-di(buthyl acrylate)aminoethyl)amine ($BA_6TREN$), tris[(2-pyridyl)methyl]amine (TPMA), 1,4,8,11-tetraazacyclotetradecane (CYCLAM), 1,4,8,11-tetraaza-1,4,8,11-tetramethylcyclotetradecane ($Me_4CYCLAM$), 4,11-dimethyl-1,4,8,11-tetraazabicyclo[6.6.2]hexadecane referred to as dimethyl cross bridged cyclam (DMCBCy), N,N,N',N'-tetrakis(2-pyridylmethyp-ethylenediamine (TPEN), diethylenetriamine (DETA), triethylenetetramine (TETA), 1,1,4,7,10,10-hexamethyltriethylenetetramine (HMTETA), 1,1,4,7,7-Pentamethyldiethylenetriamine (PMDETA), 1,1,4,7,7-Penta(methyl acrylate)diethylenetriamine ($MA_5DETA$), Glyoxal diimine-type (Gllm-R) ligands, Haddletons ligands (U.S. Pat. No. 6,310,149): N-(n-Pentyl)-2-pyridylmethanimine (n-Pen-1), N-Ethyl-2-pyridylmethanimine (Et-1), N-(n-Propyl)-2-pyridylmethanimine (n-Pr-1), N-(Cyclopropyl)-2-pyridylmethanimine (cyclo-Pr-1), N-(iso-Propyl)-2-pyridylmethanimine (iso-Pr-1), N-(n-Propyl)-2-pyridylmethanimine (n-Pr-3), N-(n-Hexyl)-2-pyridylmethanimine (n-Hex-1), N-(n-Heptyl)-2-pyridylmethanimine (n-Hep-1), N-(n-Octyl)-2-pyridylmethanimine (n-Oct-1), N-(n-Nonyl)-2-pyridylmethanimine (n-Non-1), N-(n-Octadecyl)-2-pyridylmethanimine (n-Octadec-1), n-Propyldiazabutadiene (n-Pr-2), Isopropyldiazabutadiene (iso-Pr-2), Cyclopropyldiazabutadiene (cyclo-Pr-2), 1,4-Dihexyl-2,3-diphenylmethyl-1,4-diaza-1,3-butadiene, and N-(n-Hexyl)-2-pyridylphenylmethanimine or any combination thereof.
35. The method according to any of items 13 to 34, wherein the one or more solvent(s) is selected from the group consisting of water, ethanol, methanol, ethanol/water, toluene, propanol, isopropanol, butanol, 1,1,1,3,3,3-hexafluoro-2-propanol.
36. The method according to any of items 13 to 35, wherein the one or more solvent(s) is ethanol/water or methanol/water mixed in the following ratios (volume by volume) 1:1, 1:2, 1:3, 1:4, 1:5, 2:1, 3:1, 4:1, 5:1, (0.1-1):1, 1:(0.1-1) or any other ratio.
37. The method according to any of items 13 to 36, wherein the ratio of solvent:MEA can be any ratio (volume by volume) such as (0.1-3):1, for example (0.1-0.2):1, such as (0.2-0.3):1, for example (0.3-0.4):1, such as (0.4-0.5):1, for example (0.5-0.6):1, such as (0.6-0.7):1, for example (0.7-0.8):1, such as (0.8-0.9):1, for example (0.9-1.0):1, such as (1.0-1.1):1, for example (1.1-1.2):1, such as (12-1.3):1, far example (1.3-1.4):1, such as (1.4-1.5):1, for example (1.5-1.6):1, such as (1.6-1.7):1, for example (1.7-1.8):1, such as (1.8-1.9):1, for example (1.9-2.0):1, such as (2.0-2.1):1, for example (2.1-2.2):1, such as (2.2-2.3):1, for example (2.3-2.4):1, such as (2.4-2.5):1, for example (2.5-2.6):1, such as (2.6-2.7):1, for example (2.7-2.8):1, such as (2.8-2.9):1, or any combination thereof.
38. The method according to any of items 13 to 37, wherein the ratio of MEA:solvent can be any ratio (volume by volume) such as (0.1-3):1, for example (0.1-0.2):1, such as (0.2-0.3):1, for example (0.3-0.4):1, such as (0.4-0.5):1, for example (0.5-0.6):1, such as (0.6-0.7):1, for example (0.7-0.8):1, such as (0.8-0.9):1, for example (0.9-1.0):1, such as (1.0-1.1):1, for example (1.1-1.2):1, such as (1.2-1.3):1, for example (1.3-1.4):1, such as (1.4-1.5):1, for example (1.5-1.6):1, such as (1.6-1.7):1, for example (1.7-1.8):1, such as (1.8-1.9):1, for example (1.9-2.0):1, such as (2.0-2.1):1, for example (2.1-2.2):1, such as (2.2-2.3):1, for example (2.3-2.4):1, such as (2.4-2.5):1, for example (2.5-2.6):1, such as (2.6-2.7):1, for example (2.7-2.8):1, such as (2.8-2.9):1, or any combination thereof.
39. The method according to any of items 13 to 38, wherein the ratio of solvent:MEA is 1:1 (volume by volume).
40. The method according to any of items 13 to 39, wherein the ratio of MEA:catalyst:ligand can be any ratio (mole by mole) such as (30-1000):1:(1-3), for example (30-50):1:(1-3), such as (50-100):1:(1-3), for example (100-150):1:(1-3), such as (150-200):1:(1-3), for example (200-250):1:(1-3), such as (250-300):1:(1-3), for example (300-350):1:(1-3), such as (350-400):1:(1-3), for example (400-450):1:(1-3), such as (450-500):1:(1-3), for example (500-550):1:(1-3), such as (550-600):1:(1-3), for example (600-650):1:(1-3), such as (650-700):1:(1-3), for example (700-750):1:(1-3), such as (750-800):1:(1-3), for example (800-850):1:(1-3), such as (850-900):1:(1-3), for example (900-950):1:(1-3), such as (950-1000):1:(1-3), for example (30-50):1:(1-2), such as (50-100):1:(1-2), for example (100-150):1:(1-2), such as (150-200):1:(1-2), for example (200-250):1:(1-

2), such as (250-300):1:(1-2), for example (300-350):1:(1-2), such as (350-400):1:(1-2), for example (400-450):1:(1-2), such as (450-500):1:(1-2), for example (500-550):1:(1-2), such as (550-600):1:(1-2), for example (600-650):1:(1-2), such as (650-700):1:(1-2), for example (700-750):1:(1-2), such as (750-800):1:(1-2), for example (800-850):1:(1-2), such as (850-900):1:(1-2), for example (900-950):1:(1-2), such as (950-1000):1:(1-2), for example (30-50):1:(2-3), such as (50-100):1:(2-3), for example (100-150):1:(2-3), such as (150-200):1:(2-3), for example (200-250):1:(2-3), such as (250-300):1:(2-3), for example (300-350):1:(2-3), such as (350-400):1:(2-3), for example (400-450):1:(2-3), such as (450-500):1:(2-3), for example (500-550):1:(2-3), such as (550-600):1:(2-3), for example (600-650):1:(2-3), such as (650-700):1:(2-3), for example (700-750):1:(2-3), such as (750-800):1:(2-3), for example (800-850):1:(2-3), such as (850-900):1:(2-3), for example (900-950):1:(2-3), such as (950-1000):1:(2-3), or any combination thereof.

41. The method according to any of items 13 to 40, wherein the ratio of MEA:catalyst:ligand:reducing agent can be any ratio (mole by mole) such as 1:(0.000001-0.01):(0.000001-0.01):(0.000001-0.01), such as 1:(0.00001-0.01):(0.000001-0.01):(0.000001-0.01), for example 1:(0.0001-0.01):(0.000001-0.01):(0.000001-0.01), such as 1:(0.001-0.01):(0.000001-0.01):(0.000001-0.01), for example 1:(0.000001-0.001):(0.000001-0.01):(0.000001-0.01), such as 1:(0.000001-0.0001):(0.000001-0.01):(0.000001-0.01), for example 1:(0.000001-0.0001):(0.000001-0.01):(0.000001-0.01), such as 1:(0.000001-0.01):(0.00001-0.01):(0.000001-0.01), for example 1:(0.000001-0.01):(0.0001-0.01):(0.000001-0.01), such as 1:(0.000001-0.01):(0.001-0.01):(0.000001-0.01), for example 1:(0.000001-0.01):(0.000001-0.001):(0.000001-0.01), such as 1:(0.000001-0.01):(0.000001-0.0001):(0.000001-0.01), for example 1:(0.000001-0.01):(0.000001-0.00001):(0.000001-0.01), such as 1:(0.000001-0.01):(0.000001-0.01):(0.00001-0.01), for example 1:(0.000001-0.01):(0.000001-0.01):(0.0001-0.01), such as 1:(0.000001-0.01):(0.000001-0.01):(0.001-0.01), for example 1:(0.000001-0.01):(0.000001-0.01):(0.000001-0.001), such as 1:(0.000001-0.01):(0.000001-0.01):(0.000001-0.0001), for example 1:(0.000001-0.01):(0.000001-0.01):(0.000001-0.00001), such as 1:(0.00001-0.0001):(0.000001-0.01):(0.000001-0.01), for example 1:(0.0001-0.001):(0.000001-0.01):(0.000001-0.01), such as 1:(0.000001-0.01):(0.00001-0.0001):(0.000001-0.01), for example 1:(0.000001-0.01):(0.0001-0.001):(0.000001-0.01), such as 1:(0.000001-0.01):(0.0001-0.001):(0.000001-0.01), for example 1:(0.000001-0.01):(0.001-0.01):(0.000001-0.01), such as 1:(0.000001-0.001):(0.000001-0.01):(0.000001-0.00001), for example 1:(0.000001-0.01):(0.00001-0.0001):(0.000001-0.001), such as 1:(0.000001-0.001):(0.000001-0.01):(0.0001-0.001), for example 1:(0.000001-0.001):(0.000001-0.01):(0.001-0.01) or any combinations thereof.

42. The method according to any of items 13 to 41, wherein the ratio of catalyst:ligand:reducing agent can be any ratio (mole by mole) such as 1:(1-500):(1-500), for example 1:(25-500):(1-500), such as 1:(50-500):(1-500), for example 1:(75-500):(1-500), such as 1:(100-500):(1-500), for example 1:(150-500):(1-500), such as 1:(200-500):(1-500), for example 1:(250-500):(1-500), such as 1:(300-500):(1-500), for example 1:(350-500):(1-500), such as 1:(400-500):(1-500), for example 1:(1-50):(1-500), such as 1:(1-100):(1-500), for example 1:(1-150):(1-500), such as 1:(1-200):(1-500), for example 1:(1-250):(1-500), such as 1:(1-300):(1-500), for example 1:(1-350):(1-500), such as 1:(1-400):(1-500), for example 1:(1-450):(1-500), such as 1:(50-500):(1-500), such as 1:(1-50):(1-500), for example 1:(50-100):(1-500), such as 1:(100-150):(1-500), for example 1:(150-200):(1-500), such as 1:(200-250):(1-500), for example 1:(250-300):(1-500), such as 1:(300-350):(1-500), for example 1:(350-400):(1-500), such as 1:(400-450):(1-500), for example 1:(450-500):(1-500) or any combinations thereof.

43. The method according to any of items 13 to 42, wherein the ratio of catalyst:reducing agent:ligand can be any ratio (mole by mole) such as 1:(1-500):(1-500), for example 1:(25-500):(1-500), such as 1:(50-500):(1-500), for example 1:(75-500):(1-500), such as 1:(100-500):(1-500), for example 1:(150-500):(1-500), such as 1:(200-500):(1-500), for example 1:(250-500):(1-500), such as 1:(300-500):(1-500), for example 1:(350-500):(1-500), such as 1:(400-500):(1-500), for example 1:(1-50):(1-500), such as 1:(1-100):(1-500), for example 1:(1-150):(1-500), such as 1:(1-200):(1-500), for example 1:(1-250):(1-500), such as 1:(1-300):(1-500), for example 1:(1-350):(1-500), such as 1:(1-400):(1-500), for example 1:(1-450):(1-500), such as 1:(50-500):(1-500), such as 1:(1-50):(1-500), for example 1:(50-100):(1-500), such as 1:(100-150):(1-500), for example 1:(150-200):(1-500), such as 1:(200-250):(1-500), for example 1:(250-300):(1-500), such as 1:(300-350):(1-500), for example 1:(350-400):(1-500), such as 1:(400-450):(1-500), for example 1:(450-500):(1-500) or any combinations thereof.

44. The method according to any of items 13 to 43, wherein the ratio of MEA:catalyst:ligand (equivalents; mole by mole) is (1-2000):1:(0.1-50).

45. The method according to any of items 13 to 44, wherein the one or more substrate(s) is Polymeric or organic substrates.

46. The method according to any of items 13 to 45, wherein the one or more substrate(s) is selected from the group consisting of Poly(ether ether ketone) (PEEK), Polypropylene (PP), Polyethylene (PE) (including linear low density polyethylene (LLDPE), low density polyethylene (LOPE) high density polyethylene (HDPE), ultra high molecular weight polyethylene (UHMWPE), and cross-linked polyethylene (PEX)), Poly(ethylene terephthalate) (PET), poly(propylene terephthalate (PPT), PPT/PET copolyester, Polybutylene terephthalate (PBT), Poly(vinyl chloride) (PVC), Polyamide/nylon (PA), Polycarbonate (PC), Cyclic olefin copolymer (COC), Filter paper, Cotton, Cellulose, Poly(4-vinylbenzyl chloride) (PVBC), Poly(vinylidene fluoride) (PVDF), Polystyrene (PS), Toyopearl®, Hydrogels, Polyimide (PI), 1,2-Polybutadiene (PB), Liquid silicon rubber (LSR), poly(dimethylsiloxane) (PDMS), fluoropolymers- and copolymers (e.g. poly(tetrafluoroethylene) (PTFE), Perfluoroethylene propylene copolymer (FEP), Ethylene tetrafluoroethylene copolymer (ETFE), Polyvinyl fluoride (PVF), Polyvinylidene fluoride (PVDF), Polychlorotrifluoroethylene (PCTFE)), poly(methyl methacrylate) (PMMA), Acrylonitrile butadiene styrene (ABS), styrene acrylonitrile (SAN), polyacrylonitrile (PAN), Polymethylpentene (TPX), Polyoxymethylene (POM), Polysulfone (PSU), polyetherimide (PEI), polyphenylene oxide (PPO), polyethersulfone (PES), Polyphenylene sulfide (PPS), Polyamideimide (PAI), Liquid crystal polymer (LCP), Epoxy, Polyurethane (PU), Thermoplastic elastomer (TPE), natural or synthetic rubber, polyisobutylene (PIB), polyisoprene, polyethylene-co-propylene), Kraton polymers: Poly(styrene-b-butadiene-b-styrene) (SBS), poly(styrene-b-isoprene-b-styrene) (SIS), poly(styrene-b-(ethylene/butylene)-b-styrene) (SEBS), and poly(styrene-b-(ethylene/propylene)-b-styrene) (SEPS).

47. The method according to any of items 13 to 46, wherein the one or more substrate(s) is one or more Metallic or inorganic substrates.
48. The method according to any of items 13 to 47, wherein the one or more substrate(s) is selected from the group consisting of titanium, gold, glass, silicon, geranium, quartz, silicon oxide, silica, stainless steel, diamond, and magnetic nanoparticles (e.g. $Fe_3O_4$).
49. The method according to any of items 13 to 48, wherein the one or more substrate(s) is one or more Nanoporous materials.
50. The method according to any of items 13 to 49, wherein the one or more substrate(s) is one or more membranes.
51. The method according to any of items 13 to 50, wherein the one or more substrate(s) is one or more Mesostructured cellular foam (MCF).
52. The method according to any of items 13 to 51, wherein the one or more substrate(s) is one or more singlewall or multiwall Carbon Nanotubes (SWCNT, MWCNT).
53. The method according to any of items 13 to 52, wherein the one or more substrate(s) is one or more materials with functional groups which can be used directly for attaching the initiating groups.
54. The method according to any of items 13 to 53, wherein the one or more substrate(s) is one or more materials that need to be activated before the coupling reaction of the initiator can take place.
55. A polymer coating comprising or consisting of polymer chains comprising or consisting of repeating units of 2-methoxyethyl acrylate, wherein said polymer chains are covalently bound to one or more surface(s) of one or more substrate(s) and wherein said polymer coating is obtained or obtainable by the method according to any of items 13 to 54.
56. Use of the coating according to any of items 1 to 4 and 55 for contacting one or more subject matters selected from the group consisting of one or more protein(s), one or more peptide(s), one or more pharmaceutical(s), one or more body liquids, one or more living or dead tissues, skin, fatty tissue and meat
57. The use according to item 56, wherein the one or more body liquids can be one or more body liquids selected from the group consisting of blood, blood plasma, serum, amniotic fluid, aqueous humour, cerumen, Cowper's fluid or pre-ejaculatory fluid, chyme, female ejaculate, interstitial fluid, lymph, breast milk, mucus (including nasal drainage and phlegm), pleural fluid, pus, saliva, sebum (skin oil), semen, sweat, tears, urine, vaginal secretion and vomit.
58. The use according to item 56 and 57, wherein the use results in limitation or prevention of bacterial growth.
59. The use according to item 56 and 57, wherein the use results in bacteria repellent activity.
60. Use of the device according to any of items 5 to 12.
61. The use according to any of item 56 to 60, wherein the use is for medical treatment of an individual in need thereof.
62. The use according to any of item 56 to 61, wherein the use is for medical surgery of an individual in need thereof.
63. The use according to any of item 56 to 62, wherein the use is for diagnostic analysis of an individual in need thereof.

DETAILED DESCRIPTION OF THE DRAWINGS

FIG. 1: Scheme showing the principle of Atom Transfer Radical Polymerization (ATRP). It is a controlled method which converts monomers (M) to polymers (P) by using radical polymerization. The initiators used for ATRP are commonly simple alkyl halides. A halogen atom X is transferred during the polymerization. Moreover, a catalyst system is present which consist of a transition metal ($M_t^x$) complexed by one or more ligands ($X-M_t^{x+1}$/Ligand). The catalyst provides equilibrium between the active form, $P_m^*$ and the inactive form, $P_n$-X (called the dormant state). The equilibrium is displaced towards the dormant state; therefore, the polymer chains will only be active for a short time, thus allowing for a suppression of chain termination reactions and thereby controlling the polymerization. A controlled polymerization method like ATRP will result in controlled molar masses, controlled polymer architecture, and narrow molecular weight distributions. The rate constants for the activation, deactivation, propagation and termination are: $k_{act}$, $k_{deact}$, $k_p$, and $k_t$.

FIG. 2: Structure of poly(2-methoxyethyl acrylate) (PMEA). The letter n indicates the number of repeating units.

Figure 3:
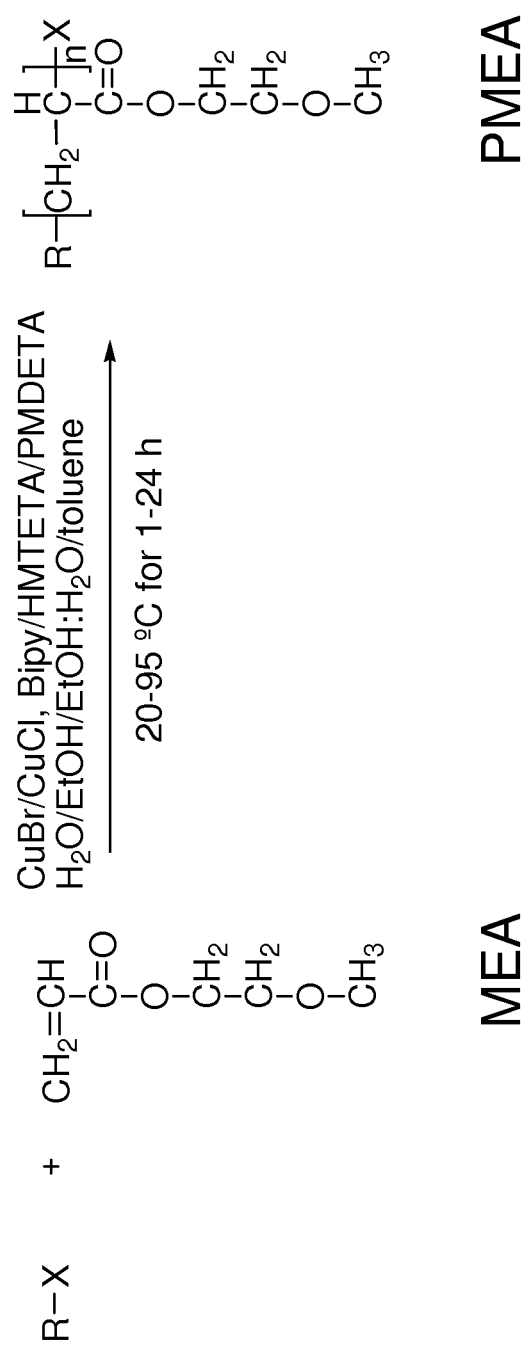
FIG. 3: Preparation of poly(2-methoxyethyl acrylate) (PMEA).

FIG. 3: Preparation of poly(2-methoxyethyl acrylate) (PMEA). Some possible conditions for the polymerization of 2-methoxyethyl acrylate (MEA) are shown. R—X is the initiator for ATRP and it consists of an alkyl halide; R is the alkyl and X is the halide (chlorine or bromine). The catalyst system for the polymerization reaction is e.g. CuBr or CuCl and one or more ligands e.g. 2,2'-bipyridine (Bipy), 1,1,4,7,10,10-hexamethyltriethylenetetramine (HMTETA), or 1,1,4,7,7-pentamethyldiethylenetriamine (PMDETA). Examples of solvents are listed water ($H_2O$) or ethanol (EtOH) or a mixture of ethanol and water (EtOH:$H_2O$) or toluene. The polymerization takes place at a temperature between 20 and 95° C. The polymerization time is between 1 and 24 hours. n is the number of repeating units in PMEA.

Figure 4:
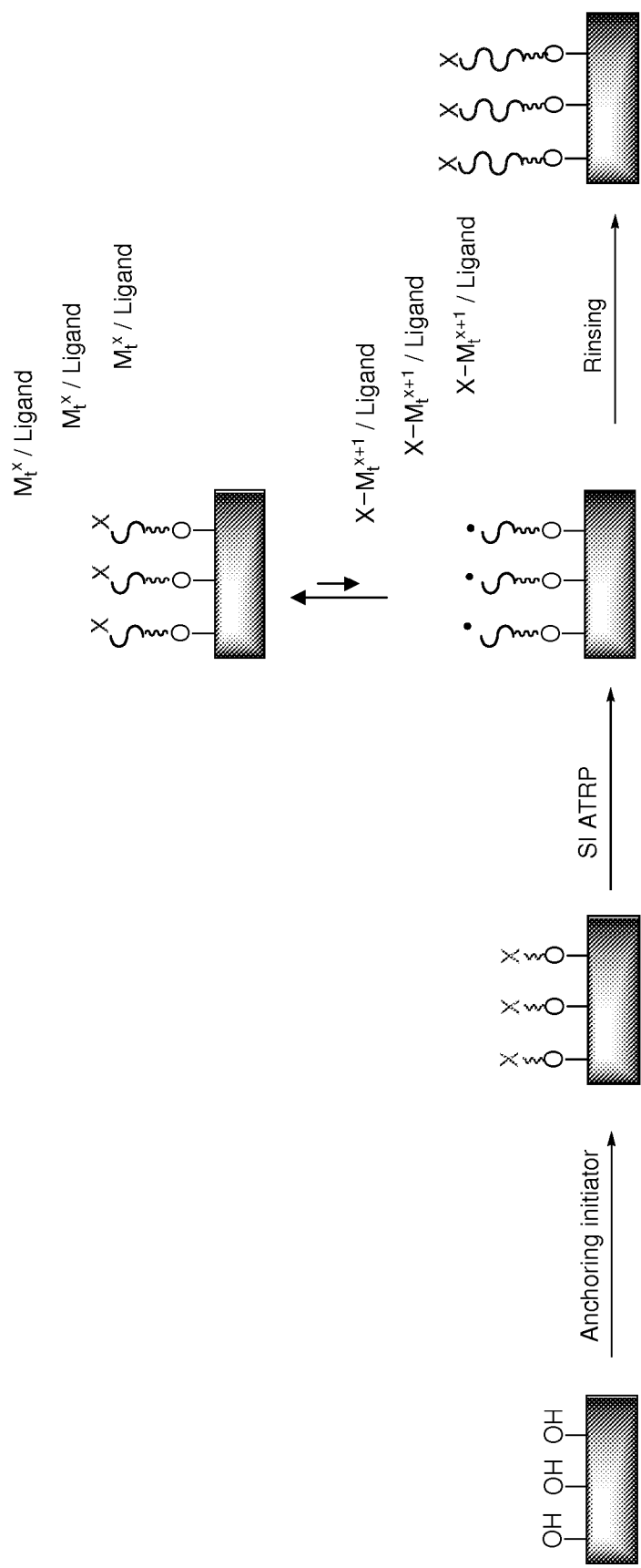
FIG. 4: Scheme showing the principle of Surface-Initiated ATRP (SI ATRP).

FIG. 4: Explanation of the technique Surface-Initiated Atom Transfer Radical Polymerization (SI ATRP). If hydroxyl groups are present they can be used for coupling the initiating groups for ATRP. Otherwise the surface of the substrate(s) needs to be activated in order to form functional groups which can be used for the coupling reaction. After anchoring of the initiating groups SI ATRP can take place. The polymerization reaction is an equilibrium between an active form and an inactive form and the inactive form is the favourable state. $M_t^x$/Ligand or $X-M_t^{x+1}$/Ligand is the catalyst system on either side of the equilibrium. When the polymer chains are active the atom X (chlorine or bromine) will bound to the catalyst. The last step is rinsing the substrate(s) to remove the catalyst system and residual monomer.

FIG. 5: Example of preparation of initiating groups on poly(ether ether ketone) (PEEK).
A) Some of the ketone groups in PEEK will be reduced to hydroxyl groups by reaction with sodium borohydride ($NaBH_4$) in dimethyl sulfoxide (DMSO) for 3 hours at 120° C. n is the number of repeating units in PEEK.
B) The hydroxyl groups on PEEK are transformed into initiating groups for SI ATRP by using 2-bromoisobutyryl bromide (Br-iBuBr) in the presence of 4-dimethylaminopyridine (DMAP) and triethylamine (TEA) in tetrahydrofurane (THF). The reaction takes place within 18 hours. When Br-iBuBr is added the temperature should be kept at 0° C. When Br-iBuBr is added the temperature in the reaction mixture will increase. The reaction mixture is left without cooling and the temperature will reach room temperature (rt.).

Figure 6:
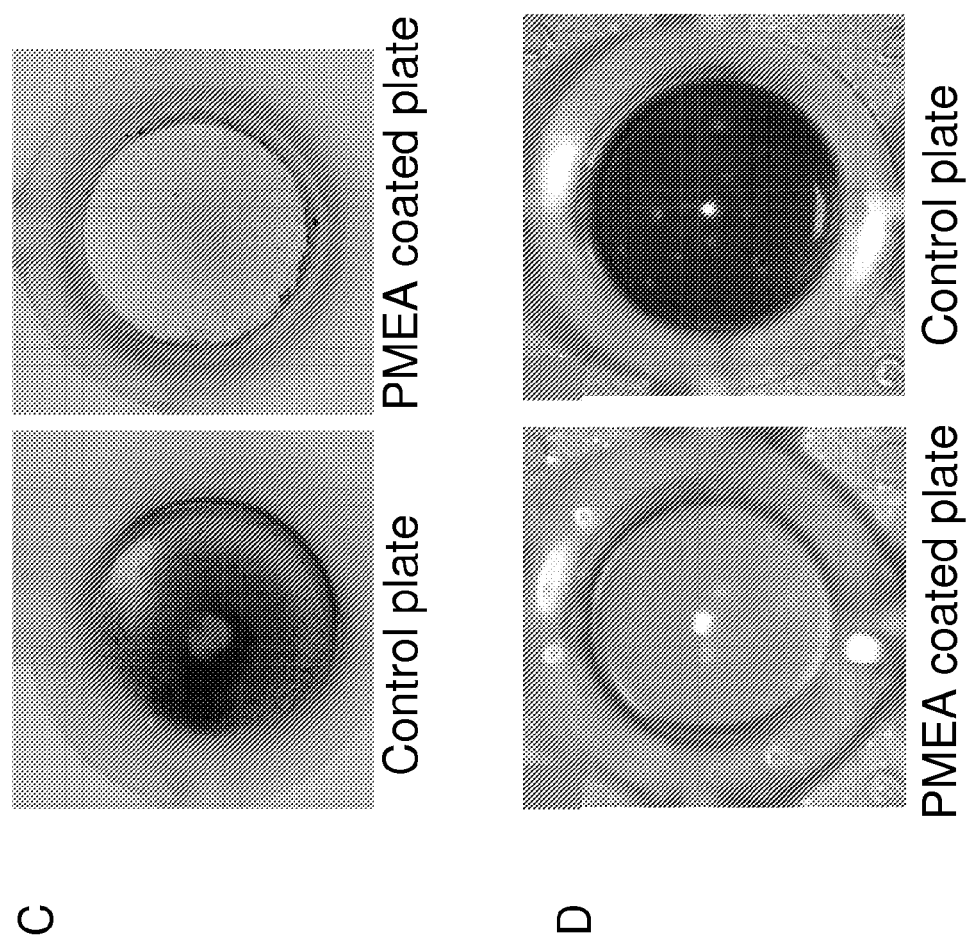
FIG. 6: Effect on bacteria attachment

FIG. 6: Effect on bacteria attachment
A) S. aureus static adherence results based on 3 hours and 24 hours on control and PMEA coated glass slides (Left picture control plate; right picture PMEA coated plate, the green dots are bacteria).

B) *Staphylococcus epidermidis* bacterial attachment on control and PMEA coated glass slides (Left picture control plate; right picture PMEA coated plate, the green dots are bacteria).

C) *Staphylococcus epidermidis* (down pictures) attachment (24 hours biofilm formation) to 96 well plates (Left picture control plate; right picture PMEA coated plate).

D) *S. aureus* incubated for 24 hours at 37° C. shows 90% reduction of *S. aureus* biofilm formation (Right picture is control plate; Left picture is PMEA coated plate).

Figure 7:
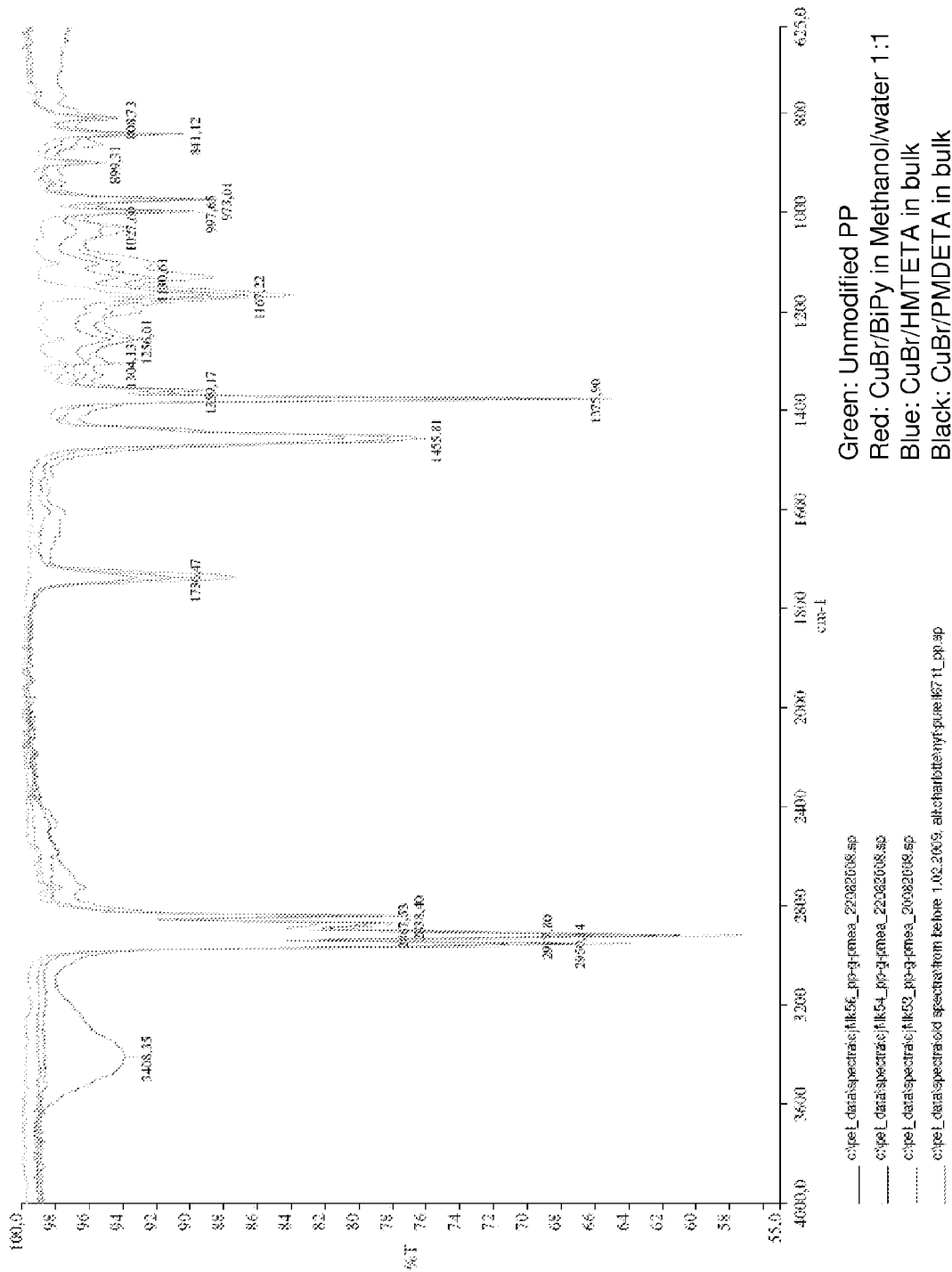
FIG. 7: Attenuated Total Reflectance Fourier Transform Infrared (ATR FT-IR) spectroscopy

FIG. 7: Attenuated Total Reflectance Fourier Transform Infrared (ATR FT-IR) spectroscopy is used to confirm that the modification of the substrate(s) has taken place. Green represents unmodified polypropylene (PP), red represents PMEA grafted from PP using CuBr/BiPy in methanol/water 1:1, blue represents PMEA grafted from PP using CuBr/HMTETA in bulk and black represents PMEA grafted from PP using CuBr/PMDETA in bulk). The PMEA coating contains e.g. ester groups and ether groups which the substrate PP does not. The carbonyl (C=O) absorption band from ester groups of PMEA is at 1736 cm$^{-1}$. Whereas the C—O stretching band from the ether groups of PMEA is at 1131 cm$^{-1}$).

FIG. 8: A) Water contact angle (WCA) measurements on substrates coated with PMEA prepared by ATRP. The advancing WCA of unmodified Liquid Silicon Rubber (LSR) is 120° and it is lowered to 69° when coated with PMEA. For low density polyethylene (LDPE) the advancing WCA is 90° and coated with PMEA it is 50°. The static WCA of poly (methyl methacrylate) (PMMA) is changed from 82° to 51° when coated with PMEA. B) Water contact angle (WCA) measurements on substrates coated with PMEA prepared by SI ATRP.

B) Water contact angle (WCA) measurements on PMEA grafted from polypropylene (PP), PP-g-PMEA by SI ATRP and unmodified PP. The measurements are made with a dynamic method which gives the advancing (adv.) and receding (rec.) contact angles. The advancing angles will be sensitive to the hydrophobic domains and receding angles will characterize the hydrophilic domains on the surface. The difference between the advancing and receding WCA can be used to help characterize surface heterogeneity and roughness. The catalyst system CuBr/HMTETA has been used to prepare this PMEA coating. The advancing WCA decreases from 106° to 78° whereas the receding WCA is reduced from 90° to 41° when MEA is polymerized from PP. In the figure advancing and receding are abbreviated adv. and rec. respectively.

Figure 9:
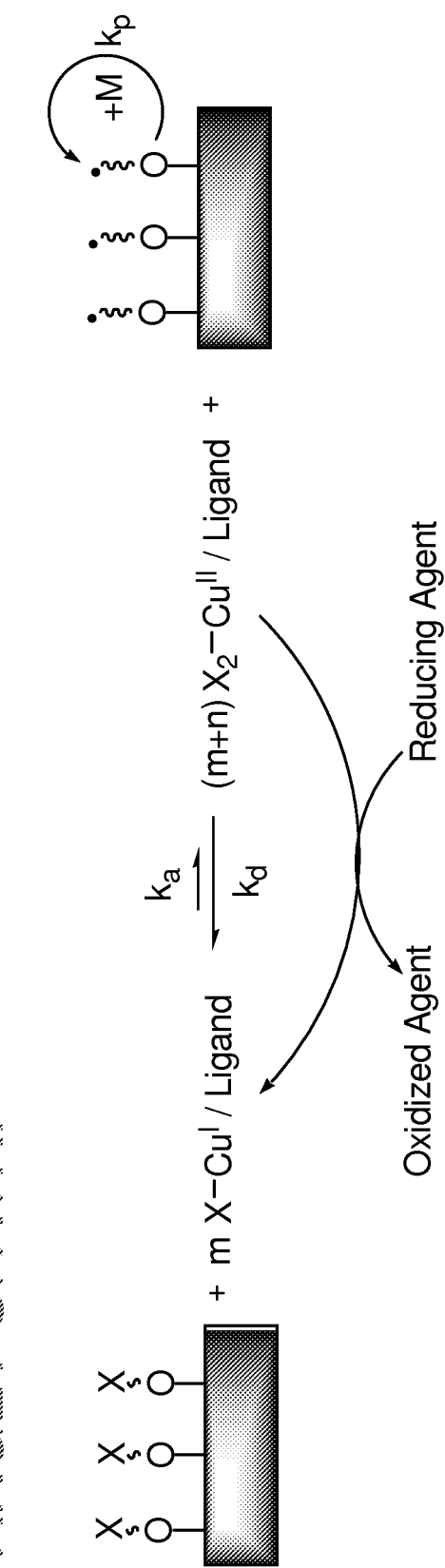
FIG. 9: Scheme showing the principle of ARGET SI ATRP

FIG. 9: Activator regenerated by electron transfer (ARGET) SI ATRP differs from SI ATRP in lower amount of catalyst and ligand and presence of reducing agent. Moreover, Cu$^{II}$ is applied instead of Cu$^{I}$. The polymerization reaction is an equilibrium between the dormant state (surface-X) and the active form (surface-*). When the chains are active another monomer is added (+M). Cu$^{II}$ is continuously reduced by the reducing agent to Cu$^{I}$. The copper catalyst contains X (chlorine or bromine) and is complexed by a ligand. The rate constants for the activation, deactivation, and propagation are: $k_a$, $k_d$, and $k_p$.

REFERENCES

[1] Wang, J. S.; Matyjaszewski, K. J. Am. Chem. Soc. 1995, 117, 5614-5615

[2] Kato, M.; Kamigaito, M.; Sawamoto, M.; Higashimura, T. Macromolecules 1995, 28, 1721-1723

[3] WO 9630421 A1 (MATYJASZEWSKI) 3 Oct. 1996

[4] Saito, N.; Motoyama, S.; Sawamoto, J. Artif. Organs 2000, 24, 547-554

[5] Suhara, H.; Sawa, Y.; Nishimura, M.; Oshiyama, H.; Yokoyama, K.; Saito, N.; Matsuda, H. Ann. Thorac. Surg. 2001, 71, 1603-1608

[6] Gunaydin, S.; Farsak, B.; Kocakulak, M.; Sari, T.; Yorgancioglu, C.; Zorlutuna, Y. Ann. Thorac. Surg. 2002, 71, 1819-1824

[7] Tanaka, M.; Mochizuki, A.; Motomura, T.; Shimura, K.; Onishi, M.; Okahata, Y. Colloid. Surface. A 2001, 193, 145-152

[8] Tanaka, M.; Mochizuki, A.; Shiroya, T.; Motomura, T.; Shimura, K.; Onishi, M.; Okahata, Y. Colloid. Surface. A 2002, 203, 195-204

[9] Bednarek, M.; Jankova, K.; Hvilsted, S. *J. Polym. Sci. Pol. Chem.* 2007, 45, 333-340

[10] Hansen, N. M. L.; Haddleton, D. M.; Hvilsted, S. *J. Polym. Sci. Pol. Chem.* 2007, 45, 5770-5780

[11] Brar, A. S.; Saini, T. Eur. Polym. J. 2007, 43, 1046-1054

[12] O. Noiset, C. Henneuse, Y.-J. Schneider, C. Marchand-Brynaert *Macromolecules* 30, 1997, 540-548.

[13] J. Huang, H. Murata, R. R. Koepsel, A. J. Rusell, K. Matyjaszewski Biomacromolecules 8, 2007, 1396-1399.

[14] F. J Xu, K. G. Neoh, E. T. Kang; Prog. Polym. Sci., 2009, 34, 719-761.

[15] C. J. Fristrup, K. Jankova, S. Hvilsted "Surface-Initiated Atom Transfer Radical Polymerization—a Technique to Develop Biofunctional Coatings" Soft Matter, 2009, 5, 4623-4634.

[16] R. Barbey, L. Lavanant, D. Paripovic, N. Schtiwer, C. Sugnaux, S. Tugulu and H.-A. Klok, *Chem. Rev.,* 2009, 109, 5437-5527.

[17] D. Roy, M. Semsarilar, J. T. Guthrie and S. Perrier, *Chem. Soc. Rev.,* 2009, 38, 1825-2148.

[18] W. A. Braunecker and K. Matyjaszewski, *Prog. Polym. Sci.,* 2007, 32, 93-146.

EXAMPLES

Example 1

Preparation of the PMEA Coating

A reactor was charged with catalyst, ligand and substrates as well as half of the solvent if the polymerization was not done in bulk. The monomer, 2-methoxyethyl acrylate (MEA) and the other half of the solvent, if any, were added to a (Schlenk) tube. After degassing 2-3 times or flushing both reactor and (Schlenk) tube with argon or nitrogen for 15 to 60 minutes, the content of the Schlenk tube (MEA or MEA and solvent) was transferred to the reactor with the substrates and catalyst system. Subsequently, the polymerization took place at an elevated temperature under inert atmosphere (e.g. nitrogen or argon gas).

The solvent could also be added to one of the tubes instead of dividing it into the two tubes. In case the ligand is not a liquid; some solvent or monomer should be used to wet the catalyst system in order to avoid removal of the catalyst system during degassing. If monomer is used for the wetting; catalyst and ligand should not be in the same reactor/tube.

TABLE 1

Polymerization of MEA, solvent:monomer (monomer is M or MEA) ratio is by volume

| Solvent | Solvent:monomer | Ligand | M:CuX:L Monomer:catalyst: ligand | Temperature, °C. | Time, h |
|---|---|---|---|---|---|
| Ethanol/water 1:1 | (0.1-2):1 | Elpy | (30-1000):1:(1-3) | 35 | 0.3-22 |
| Methanol/water 1:1 | (0.1-2):1 | Bipy | (30-1000):1:(1-3) | 35 | 0.3-22 |
| Ethanol/water 3:1 | (0.1-2):1 | Bipy | (30-1000):1:(1-3) | 35 | 0.3-3.3 |
| Ethanol | (0.1-2):1 | Bipy | (30-1000):1:(1-3) | 70 | 5-26 |
| — | — | PMDETA | (30-1000):1:(1-2) | 90 | 1-3 |
| — | — | HMTETA | (30-1000):1:(1-2) | 90-95 | 1-4 |
| Toluene | (0.1-1):1 | HMTETA | (30-1000):1:(1-2) | 90 | 1-4 |
| — | — | HMTETA | (30-1000):1:(1-2) | 50 | 2-26 |
| — | — | PMDETA | (30-1000):1:(1-2) | 50 | 2-19 |

Monomer = MEA
M:CuX:L = Monomer:catalyst:L (equivalents),
X = Br or Cl
Bipy: 2,2'-Bipyridine
PMDETA: 1,1,4,7,7-Pentamethyldiethylenetriamine
HMTETA: 1,1,4,7,10,10-Hexamethyltriethylenetetramine Examples of catalyst systems comprise catalysts, wherein the metal in the catalyst is copper. However, the metal in the catalyst does not necessarily have to be copper. Other catalysts in combination with various ligands can be used.

Example 2

SI ATRP of MEA

Three polypropylene (PP) plates (approximately 1×1 cm each) with initiating groups (see modification step of PP in Example 3) for ATRP, CuBr (0.0299 g), PMDETA (43.16 μL), and a stirring bar were added to one Schlenk tube. MEA (4 mL) was added to another Schlenk tube. After three freeze-pump-thaw cycles of each tube; MEA was transferred to the other tube. The charged Schlenk tube was immersed in an oil bath and heated to 50° C. Different polymerization times have been used (see Table 2).

TABLE 2

Examples of ATRP of MEA

| Solvent | Solvent:monomer | Ligand | M:CuBr:lig. | Temperature, °C. | Time |
|---|---|---|---|---|---|
| Ethanol/water 1:1 | 1:1 | Bipy | 139:1:2 | 35 | 22 h and 20 min. |
| Methanol/water 1:1 | 1:1 | Bipy | 152:1:2 | 35 | 22 h |
| Ethanol/water 3:1 | 1:1 | Bipy | 150:1:1 | 35 | 200 min. |
| Ethanol | 1:1 | Bipy | 150:1:1 | 70 | 1700 min. |
| — | — | PMDETA | 150:1:1 | 90 | 60-120 min. |
| — | — | HMTETA | 150:1:1 | 90-95 | 220 min. |
| Toluene | 1:1 | HMTETA | 150:1:1 | 90 | 220 min. |
| — | — | HMTETA | 152:1:1 | 50 | 2-26 h |
| — | — | PMDETA | 152:1:1 | 50 | 2-19 h |

Monomer = MEA
M:CuX:L = Monomer:catalyst:ligand (equivalents),
X = Br or Cl
Bipy: 2,2'-Bipyridine
PMDETA: 1,1,4,7,7-Pentamethyldiethylenetriamine
HMTETA: 1,1,4,7,10,10-Hexamethyltriethylenetetramine Example 3

SI ATRP

A none limiting example of SI ATRP is disclosed herein below. PEEK contains ketones which can be reduced to hydroxyl groups by $NaBH_4$ in dimethyl sulfoxide (DMSO) [10] (see FIG. 5A).

Subsequently, initiating groups can be formed by modifying the hydroxyl groups with 2-bromoisobutyryl bromide (Br-iBuBr) in the presence of 4-dimethylaminopyridine (DMAP) and triethylamine (TEA) in tetrahydrofurane (THF) (see FIG. 5B).

PP is on the other hand a very inert material which can be activated by e.g. irradiation, plasma treatment etc. One procedure is immersion of PP in a solution of toluene and 4-hydroxy benzophenone (BP-iBuBr) followed by UV irradiation at 365 nm. C—C bonds will be formed between PP and the carbon marked with a star (*) [11] (see FIG. 5C).

Then SI-ATRP can be performed with e.g. MEA using the conditions described above (see FIG. 5D). For other none limiting examples see [12-13].

Example 4

Effect on Bacteria Attachment

Bacteria test with *Staphylococcus aureus* (*S. aureus*), *Staphylococcus epidermidis* and *Pseudomonas aeruginosa*, have shown that the bacterial attachment is substantially reduced by the PMEA coating disclosed in the present invention. Moreover *Staphylococcus epidermidis* biofilm formation is reduced by 95% (see FIG. 6A-D).

FIG. 6A shows the *S. aureus* static adherence results based on 3 hours and 24 hours on control and PMEA coated glass slides, respectively (FIG. 6A). This demonstrates less adherence of *S. aureus* to the PMEA coated glass slide.

FIG. 6B shows *Staphylococcus epidermidis* bacterial attachment on control and PMEA coated glass slides, respectively (FIG. 6B). The PMEA coated plate has less bacteria attachment.

FIG. 6C shows *Staphylococcus epidermidis* (down pictures) attachment (24 hours biofilm formation) to 96 well plates (FIG. 6C). The PMEA coating has less attachment of *Staphylococcus epidermidis*.

*S. aureus* incubated for 24 hours at 37° C. shows 90% reduction of *S. aureus* biofilm formation for the PMEA coated plate compared to the control plate (FIG. 6D).

Example 5

Attenuated Total Reflectance Fourier Transform Infrared (ATR FT-IR) Spectroscopy Attenuated Total Reflectance Fourier Transform Infrared (ATR FT-IR) spectroscopy of the PMEA coating according to the present invention (see result in FIG. 7; Green represents Unmodified PP, Red represents PMEA grafted from PP using CuBr/BiPy in Methanol/water 1:1, Blue represents PMEA grafted from PP using CuBr/HMTETA in bulk and Black represents PMEA grafted from PP using CuBr/PMDETA in bulk) and FIG. 8A).

Attenuated Total Reflectance (ATR) Fourier Transform Infrared (FTIR) spectra were obtained using a Spectrum One spectrometer from Perkin Elmer which was equipped with a universal ATR sample accessory.

Grafting of PMEA from PP by SI-ATRP was confirmed with ATR FT-IR. The carbonyl (C=O) absorption band at 1736 $cm^{-1}$ indicated the presence of ester groups from PMEA. Moreover, a C—O stretching band was seen from the ether group (1131 $cm^{-1}$) of PMEA (see FIG. 7). When the substrate and the coating do not contain the same functional groups ATR FTIR spectroscopy can be used. The absorption bands in the spectra will give information about the functional groups which are present. The technique will measure about 2-3 µm into the sample; therefore, the spectra will contain absorption bands from both the coating and the substrate.

Example 6

Results from Water Contact Angle (WCA) Measurements

Figure 8A:
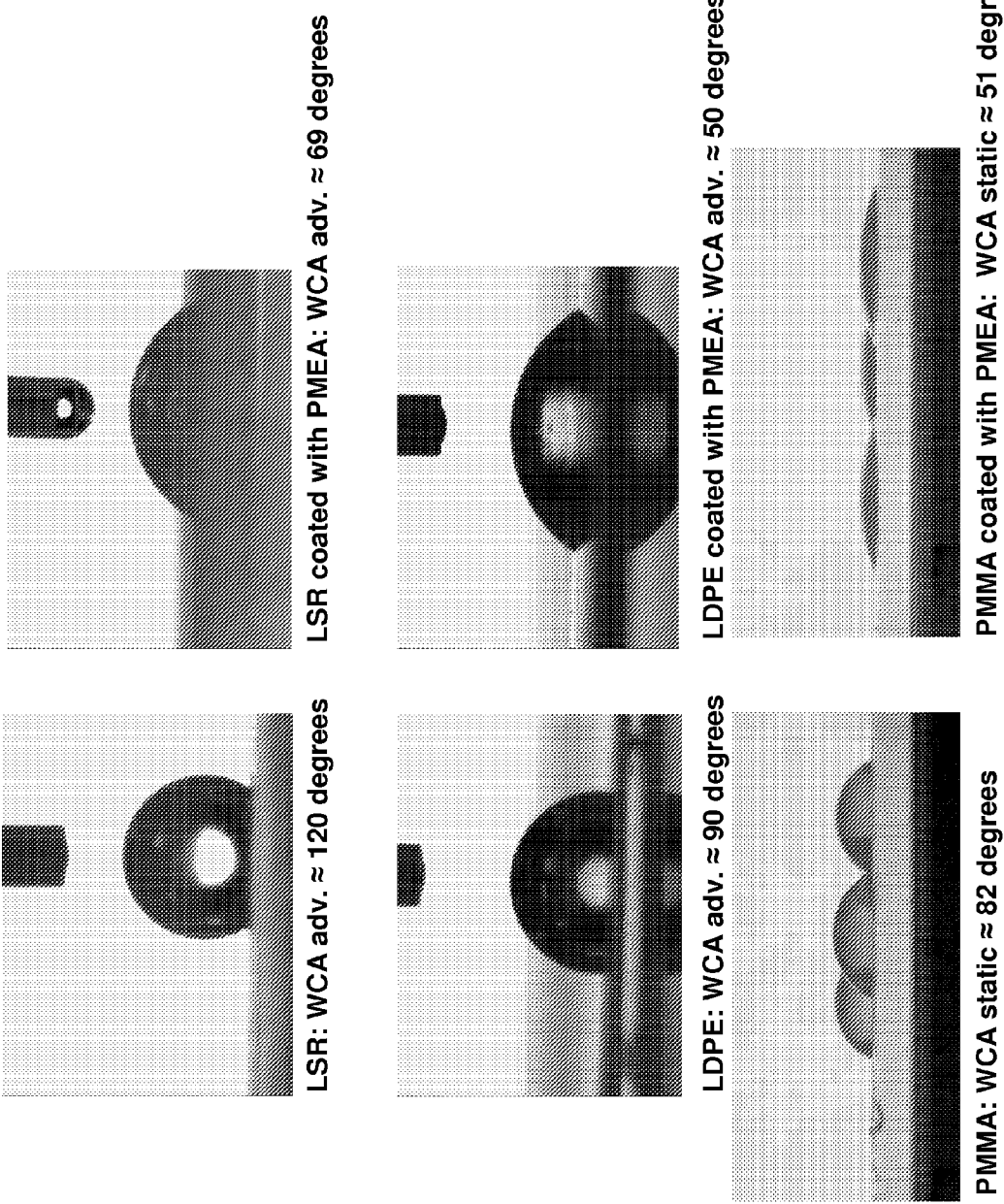
FIG. 8: Water contact angle (WCA) measurements

The water contact angle (WCA) measurements on PMEA prepared by ATRP and coated on different substrates are shown in FIG. 8A. The method can be used to determine the hydrophilicity of PMEA coated substrate. The measurements shown are made with either a dynamic method which gives advancing and receding angles or a static method which only gives one value. When testing with water, advancing angles will be sensitive to the hydrophobic domains and receding angles will characterize the hydrophilic domains on the surface. The difference between the advancing and receding CA can be used to help characterize surface heterogeneity and roughness.

Figure 8B:
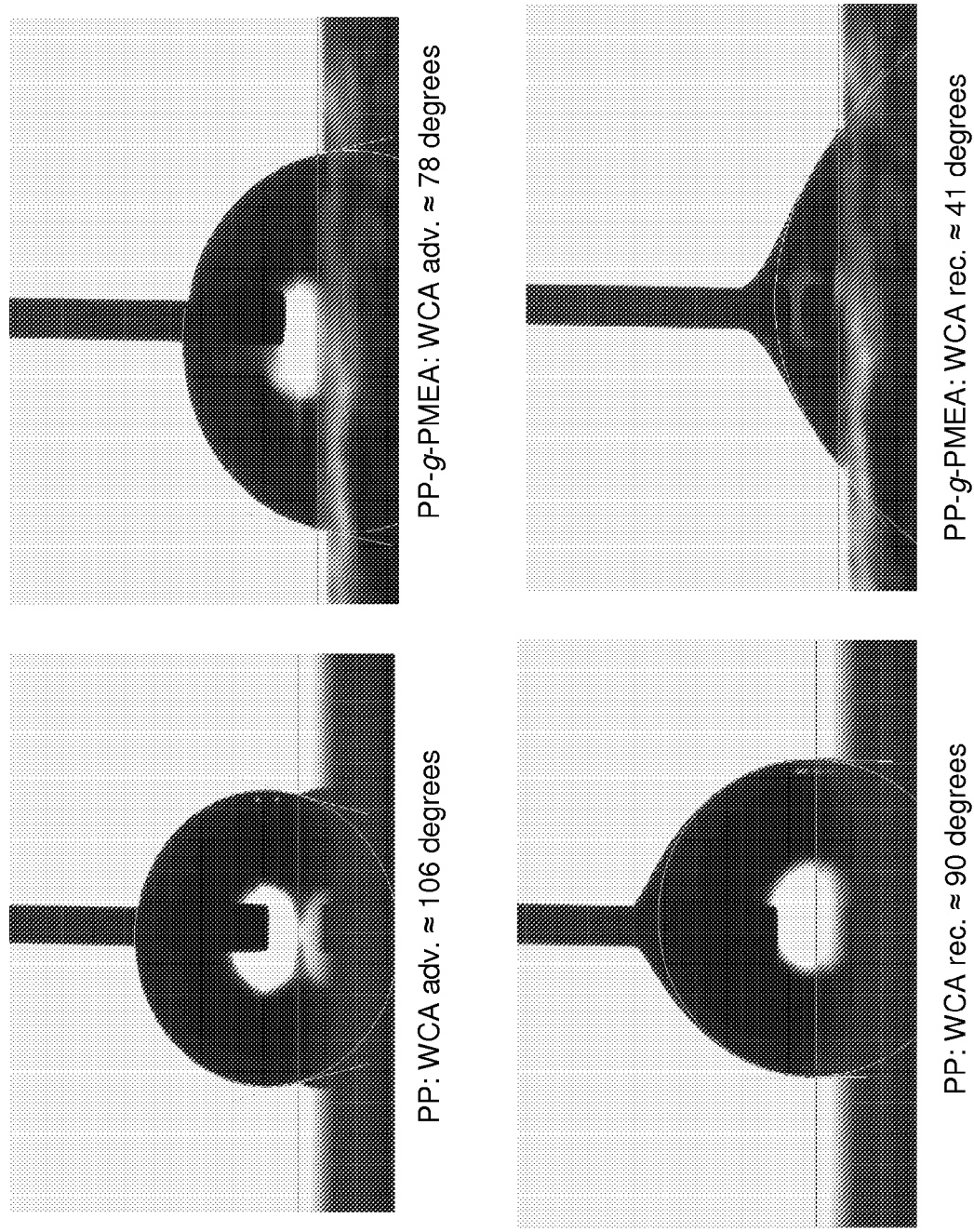

The measurements in FIG. 8B were made on OCA20 Contact Angle System from Dataphysics with a temperature controller. The temperature was set to 25° C. A dynamic method called "sessile drop (needle in)" was used and the WCAs were computed using "Ellipse Fitting". PMEA has been grafted from polypropylene (PP) using SI-ATRP. Different catalyst systems have been used which have resulted in different water contact angles (see table below). The PMEA coated PP (PP-g-PMEA) in italic is used for the pictures in FIG. 8B.

| Material | Catalyst system | WCA advancing, $^D$ | WCA receding, $^D$ |
|---|---|---|---|
| PP unmodified | — | 106 ± 1 | 90 ± 1 |
| PP-g-PMEA | CuBr/Bipy | 103 ± 1 | 66 ± 3 |
| PP-g-PMEA | CuBr/HMTETA | 78 ± 1 | 41 ± 2 |
| PP-g-PMEA | CuBr/PMDETA | 75 ± 1 | 36 ± 3 |

Bipy: 2,2'-Bipyridine
PMDETA: 1,1,4,7,7-Pentamethyldiethylenetriamine
HMTETA: 1,1,4,7,10,10-Hexamethyltriethylenetetramine The WCAs are lowered when PMEA is grafted from the surface of PP substrates. Especially the receding WCAs are lower for the modified PP compared with the unmodified PP due to changes in the hydrophilicity. It is shown in the table that the polymerization conditions e.g. the catalyst systems have an influence on the WCAs of PP-g-PMEA as they can affect the grafting densities and chain lengths.

Example 7

ARGET SI ATRP of MEA with Low Catalyst Concentration

ARGET SI ATRP of MEA was performed from 188 PP plates (3.5×0.6×0.1 cm each). The PP plates were functionalized with initiating groups for ATRP (see example 3) prior to the grafting of PMEA. The plates, $CuBr_2$ (21.1 mg), $Me_6TREN$ (213.6 mg), L-ascorbic acid (164.0 mg), 120 mL anisole, and a stirring bar were added to a round-bottom flask. MEA (180 mL) was added to another round-bottom flask. Two freeze-pump-thaw cycles were carried out for each flask and MEA was transferred to the other flask. After one freeze-pump-thaw cycle for the charged round-bottom flask; the polymerization was started by immersion into a 60° C. oil bath. The polymerization time was 20 hours. Washing of the modified plates consisted of three steps each for one hour 1) hexane, 2) 1:1 water/methanol, and 3) 5:1 water/ethanol.

The invention claimed is:
1. A method for making a polymer coating comprising straight polymer chains consisting of repeating units of 2-methoxyethyl acrylate (MEA), wherein said straight polymer chains are bound to one or more surface(s) of one or more polymeric substrate(s) via one or more covalent bonds at an end of each of the straight polymer chains; said method comprising polymerizing said MEA from one or more polymeric surfaces by surface-initiated atom transfer radical polymerization (SI ATRP) thereby producing a polymer coating com- prising straight polymer chains consisting of repeating units of 2-methoxyethyl acrylate (MEA), wherein said straight polymer chains are bound to one or more surface(s) of one or more polymeric substrate(s) via one or more covalent bonds at an end of each of the straight polymer chains, wherein the polymer coating inhibits bacterial growth on the one or more surfaces by more than 50% compared to an uncoated surface.

2. The method according to claim 1, wherein the method comprises the steps of:
   i) binding initiator groups covalently to one or more surface(s) of said polymeric substrate, producing covalently bound initiator groups,
   ii) adding one or more catalyst(s), one or more ligand(s), 2-methoxyethyl acrylate and optionally one or more solvent(s) to a reaction container comprising one or more substrate(s) with one or more surface(s) comprising said covalently bound initiator groups,
   iii) polymerizing said MEA monomers to form 2-methoxyethyl acrylate polymer (PMEA) chains covalently bound to said initiator groups, and optionally,
   iv) adding one or more reducing agents;
thereby making a PMEA-coated surface.

3. The method according to claim 1, wherein the method comprises the steps of:
   i) binding initiator groups covalently to one or more surface(s) of said polymeric substrate,
   ii) adding one or more catalyst(s), one or more ligand(s) and optionally one or more solvent(s) to a first reaction container comprising one or more substrate(s) with one or more surface(s) comprising said initiator groups,
   iii) adding 2-methoxyethyl acrylate and optionally one or more solvent(s) to a second reaction container,
   iv) optionally removing oxygen from said first reaction container and/or said second reaction container by degassing and/or flushing and/or one or more freeze-pump-thaw cycles,
   v) transferring the content of said second container to said first container,
   vi) polymerizing said MEA monomers to form 2-methoxyethyl acrylate polymer chains covalently bound to said initiator groups, and optionally
   vi) adding one or more reducing agents,
thereby making a PMEA-coated surface.

4. The method according to claim 1, wherein the method comprises the steps of:
   i) binding initiator groups covalently to one or more surface(s) of said polymeric substrate,
   ii) adding one or more catalyst(s), 2-methoxyethyl acrylate and optionally one or more solvent(s) to a first reaction container comprising one or more substrate(s) with one or more surface(s) comprising said initiator groups,
   iii) adding one or more ligand(s) and optionally one or more solvent(s) to a second reaction container,
   iv) optionally removing oxygen from said first reaction container and/or said second reaction container by degassing and/or flushing and/or one or more freeze-pump-thaw cycles,
   v) transferring the content of said second container to said first container,
   vi) polymerizing said MEA monomers to form 2-methoxyethyl acrylate polymer chains covalently bound to said initiator groups, and optionally
   vii) adding one or more reducing agents,
thereby making a PMEA coating covalently attached to the surface of the substrate.

5. The method according to claim 1, wherein the method comprises the steps of:
   i) binding initiator groups covalently to one or more surface(s) of said polymeric substrate,
   ii) adding one or more catalyst(s), one or more ligand(s), 2-methoxyethyl acrylate and optionally one or more solvent(s) to a reaction container comprising one or more substrate(s) with one or more surface(s) comprising said initiator groups,
   iii) optionally removing oxygen from said reaction container by degassing and/or flushing and/or one or more freeze-pump-thaw cycles,
   iv) polymerizing said MEA monomers to form 2-methoxyethyl acrylate polymer chains covalently bound to said initiator groups, and optionally
   v) adding one or more reducing agents,
thereby making a PMEA-coated surface.

6. The method according to claim 1, wherein the method comprises the steps of:
   i) adding one or more catalyst(s), one or more ligand(s), and optionally one or more solvent(s) to a reaction container comprising one or more polymeric substrate(s),
   ii) optionally removing oxygen from said reaction container by degassing and/or flushing and/or one or more freeze-pump-thaw cycles,
   iii) adding 2-methoxyethyl acrylate and optionally one or more solvent(s) to said reaction container after oxygen has been removed from said reaction container,
   iv) polymerizing said MEA monomers to form 2-methoxyethyl acrylate polymer chains covalently bound to said initiator groups, and optionally
   v) adding one or more reducing agents,
and thereby preparing a PMEA-coated surface.

7. The method according to claim 1, wherein the method comprises the steps of:
   i) adding one or more catalyst(s), 2-methoxyethyl acrylate, and optionally one or more solvent(s) to a reaction container comprising one or more polymeric substrate(s),
   ii) optionally removing oxygen from said reaction container by degassing and/or flushing and/or one or more freeze-pump-thaw cycles,
   iii) adding one or more ligand(s) and optionally one or more solvent(s) to said reaction container after oxygen has been removed from said reaction container,
   iv) polymerizing said MEA monomers to form 2-methoxyethyl acrylate polymer chains covalently bound to said initiator groups, and optionally
   v) adding one or more reducing agents,
and thereby preparing a PMEA-coated surface.

8. The method according to claim 1, wherein the method comprises the steps of:
   i) adding one or more catalyst(s), 2-methoxyethyl acrylate, one or more ligand(s) and optionally one or more solvent(s) to a reaction container under inert atmosphere,
   ii) optionally removing oxygen from said reaction container by degassing and/or flushing and/or one or more freeze-pump-thaw cycles,
   iii) adding one or more substrates to said reaction container under inert atmosphere,
   iv) polymerizing said MEA monomers to form 2-methoxyethyl acrylate polymer chains covalently bound to said initiator groups, and optionally
   v) adding one or more reducing agents,
and thereby preparing a PMEA-coated surface.

9. A method according to claim 1, wherein the polymeric substrate(s) is organic.

* * * * *